United States Patent
Bellemare et al.

(10) Patent No.: US 9,778,158 B2
(45) Date of Patent: Oct. 3, 2017

(54) SCRATCH TESTING APPARATUS AND METHODS OF USING SAME

(71) Applicant: Massachusetts Materials Technologies LLC, Weston, MA (US)

(72) Inventors: Simon Claude Bellemare, Weston, MA (US); Steven D. Palkovic, Boston, MA (US); Simon Normand, Cambridge, MA (US)

(73) Assignee: Massachusetts Materials Technologies LLC, Cambridge, MA (US)

( * ) Notice: Subject to any disclaimer, the term of this patent is extended or adjusted under 35 U.S.C. 154(b) by 522 days.

(21) Appl. No.: 14/310,611

(22) Filed: Jun. 20, 2014

(65) Prior Publication Data

US 2014/0373608 A1    Dec. 25, 2014

Related U.S. Application Data

(60) Provisional application No. 61/837,724, filed on Jun. 21, 2013.

(51) Int. Cl.
   *G01N 3/46* (2006.01)
(52) U.S. Cl.
   CPC ...................... *G01N 3/46* (2013.01)
(58) Field of Classification Search
   CPC .......................................... G01N 3/46
   See application file for complete search history.

(56) References Cited

U.S. PATENT DOCUMENTS

| | | | | |
|---|---|---|---|---|
| 5,686,652 A * | 11/1997 | Pfund | ...................... | G01M 7/08 73/12.04 |
| 6,520,004 B1 | 2/2003 | Lin | | |
| 6,718,820 B2 * | 4/2004 | Kwon | ...................... | G01N 3/48 73/81 |
| 7,302,831 B2 * | 12/2007 | Moyse | ................... | G01N 19/02 73/81 |
| 2004/0011119 A1 | 1/2004 | Jardret et al. | | |
| 2006/0174699 A1 | 8/2006 | Hicks et al. | | |

(Continued)

FOREIGN PATENT DOCUMENTS

| JP | 2002-506221 A | 2/2002 |
|---|---|---|
| WO | WO 02/16907 A1 | 2/2002 |

OTHER PUBLICATIONS

International Searching Authority, International Search Report—International Application No. PCT/US2014/043498, dated Aug. Oct. 16, 2014, together with the Written Opinion of the International Searching okuthority, 17 pages.

(Continued)

*Primary Examiner* — Ryan Walsh
(74) *Attorney, Agent, or Firm* — Sunstein Kann Murphy & Timbers LLP

(57) ABSTRACT

Provide in one embodiment is an apparatus, comprising an indentor wherein a tip thereof is configured to engage a sample surface, a surface-referencing device configured to establish the position of the indentor relative to the sample surface, a drive mechanism configured to move the indentor along the sample surface to form a scratch, and a measurement device configured to measure at least one of (i) a pile-up height of sample material removed from the scratch and (ii) a width of the scratch.

27 Claims, 28 Drawing Sheets

(56) References Cited

U.S. PATENT DOCUMENTS

| | | | |
|---|---|---|---|
| 2006/0191327 A1* | 8/2006 | Yang | G01N 3/46 73/81 |
| 2007/0227236 A1 | 10/2007 | Bonilla et al. | |
| 2008/0028840 A1* | 2/2008 | Smith | G01N 3/42 73/81 |
| 2009/0145208 A1 | 6/2009 | Coudert et al. | |
| 2009/0260415 A1* | 10/2009 | Suarez-Rivera | G01N 3/46 73/7 |

OTHER PUBLICATIONS

European Patent Office, Extended European Search Report—Application No. 14814061.9 dated Jan. 30, 2017, 8 pages.

\* cited by examiner

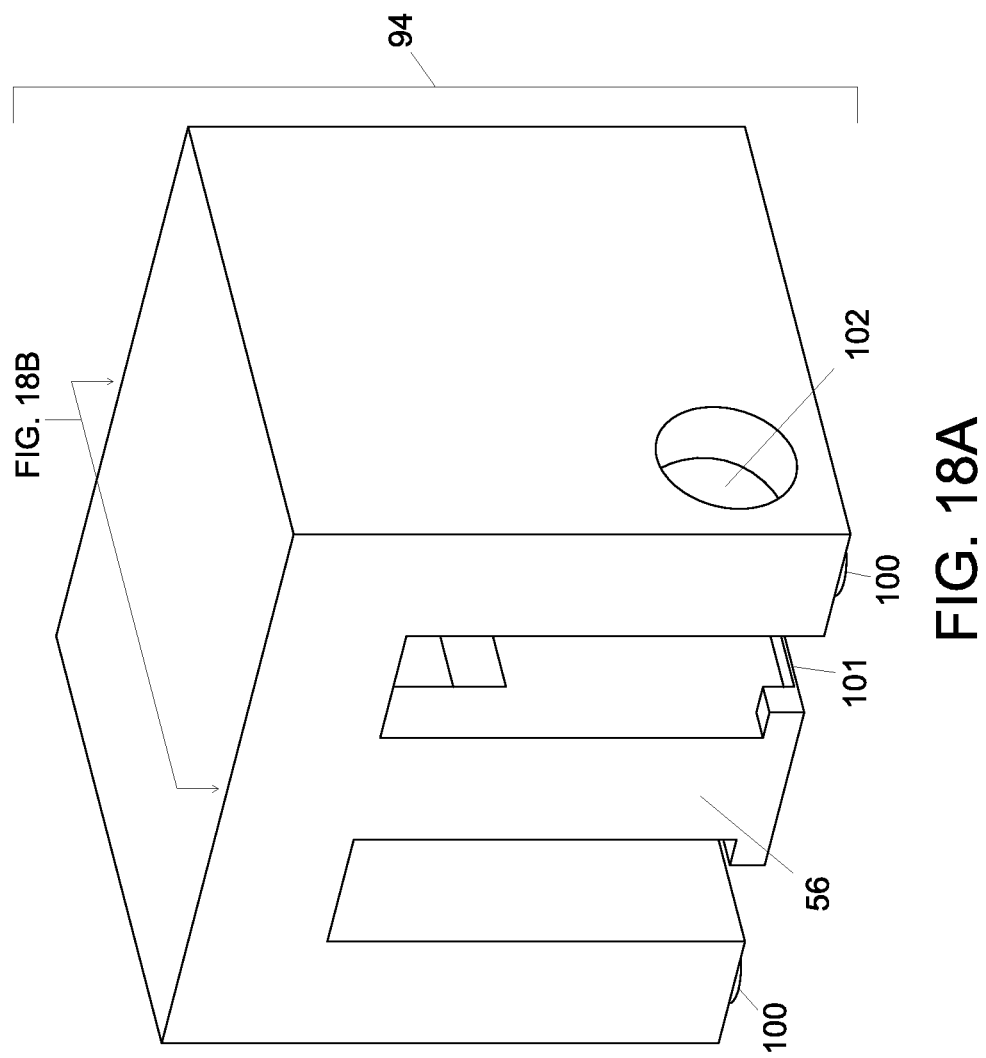

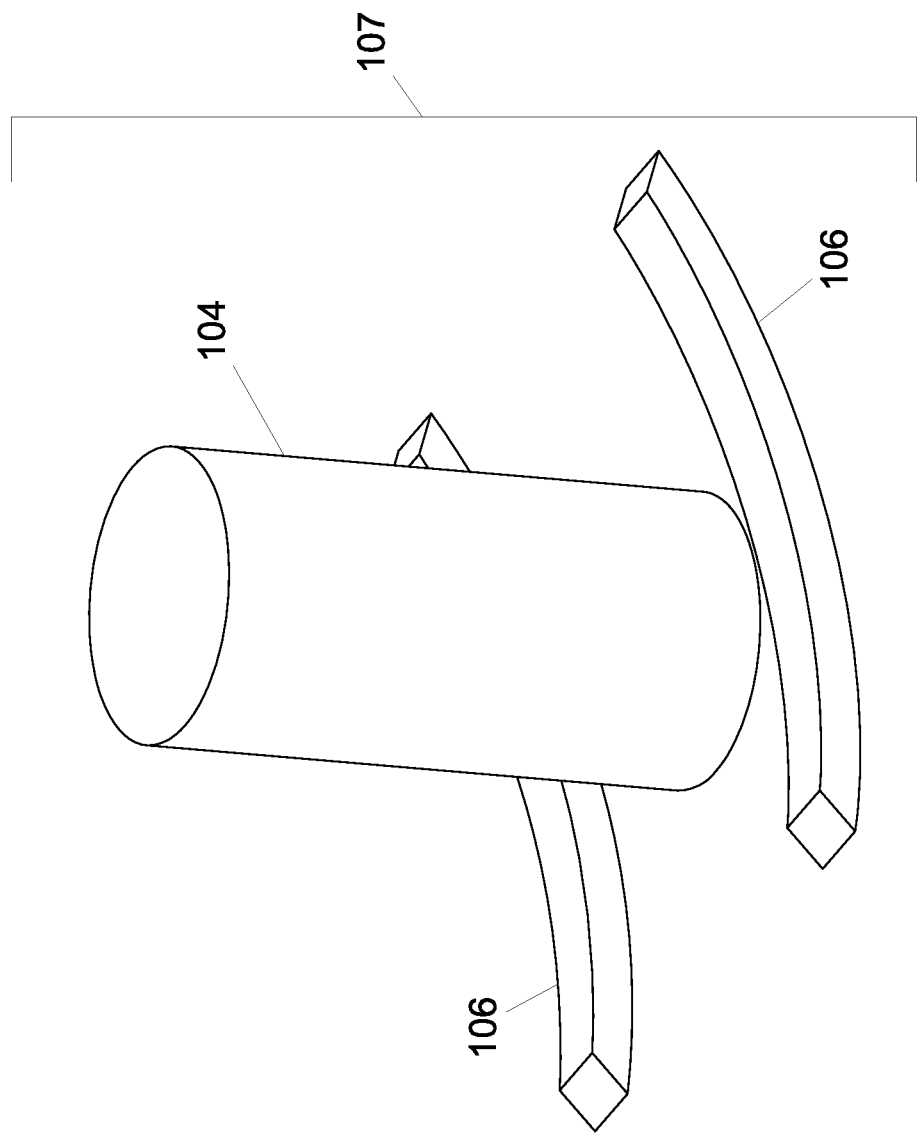

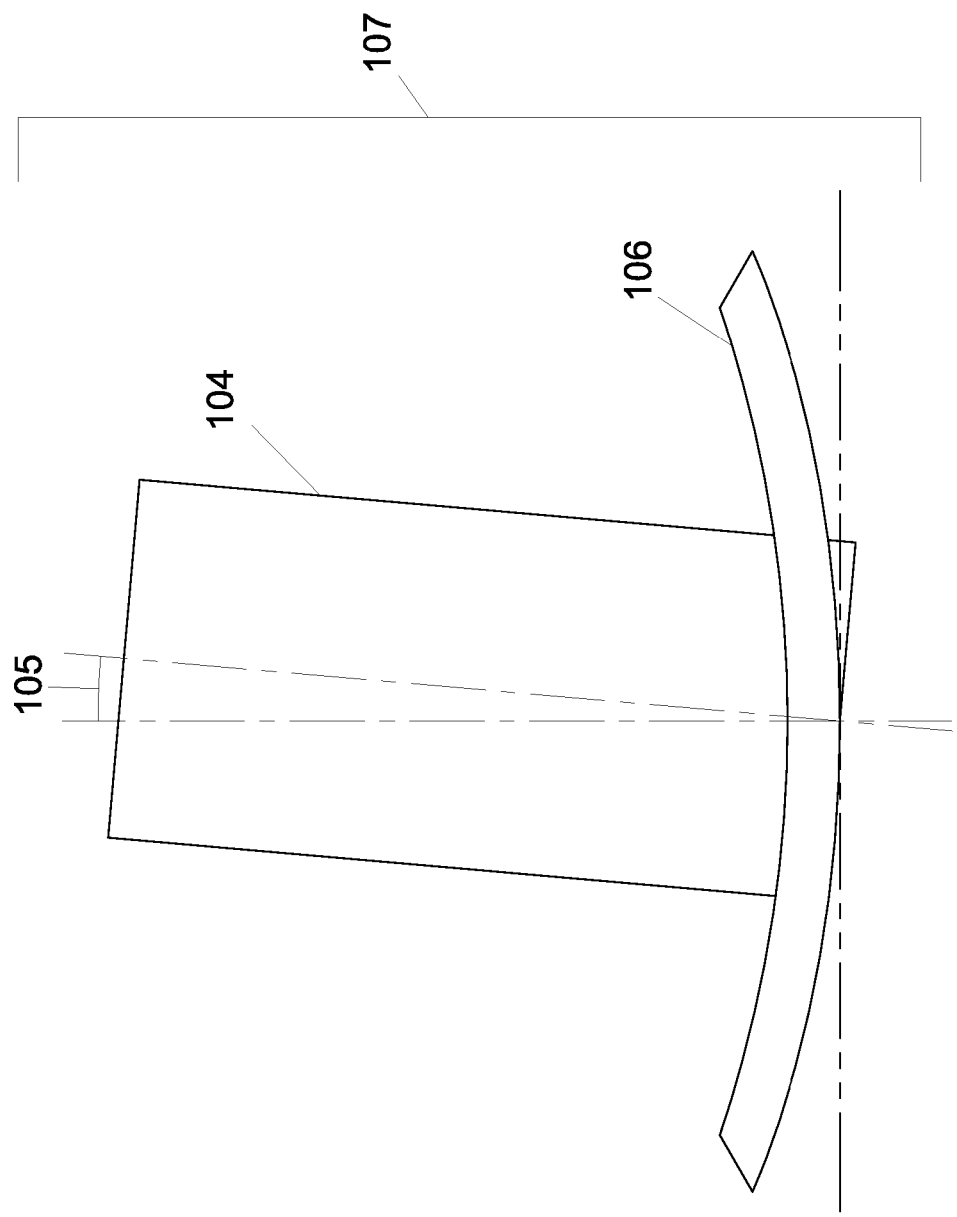

SCRATCH TESTING APPARATUS AND METHODS OF USING SAME

CROSS-REFERENCE TO RELATED PATENT APPLICATIONS

This application claims priority from U.S. Provisional Application Ser. No. 61/837,724, filed Jun. 21, 2013, which is incorporated herein by reference in its entirety.

BACKGROUND

Engineers utilize knowledge of mechanical properties to determine the strength, durability, and safety of load bearing structures. Non-destructive testing (NDT) methods are appealing because they allow for the determination of these properties without damaging the structure as a whole during testing. They are used extensively in quality control of new manufacturing and diagnostics of existing structures.

Current industrial non-destructive techniques are limited to measuring the hardness of a material by indentation, which provides an index of a material's resistance to penetration by a hard indentor. Although indentation testing is widely used, it provides limited and uncertain information that often may not be used by engineers to confidently predict the existing strength or remaining life of structures.

Scratch testing has historically been used in a similar manner to indentation hardness measurement. The Moh's hardness scale is a measure of scratch hardness that has been used for over a century to evaluate resistance of materials to scratching. This test provides a qualitative measure of strength that only allows for comparisons between known materials. However, implementing this methodology with existing technology necessitates sophisticated equipment and time-consuming operations to perform the tests and collect the scratch response of the material.

Currently, scratch testing is used to measure the strength of thin-films and coatings. This is done by using a hard tip to scratch the material while controlling the load being applied until failure occurs. This testing method is limited to select applications where materials utilize thin-films or coatings. This restriction makes the technology unsuited for assessing mechanical properties of common engineering materials.

Other scratch testing devices and systems have been developed, but their underlying test apparatus are either too complex or not sufficiently accurate for broad commercial use. Although the scientific basis for predicting yield strength and ductility of metals through a scratch test has been proven, the existing testing systems provide only partial solutions for evaluating mechanical properties.

The use of scratch testing in industrial applications is limited due to several factors, including the complexity of controlling and measuring the numerous parameters associated with the test, as well as the lack of integrated and affordable equipment and resources to perform the test and analyze the data. The preexisting test techniques involve controlling the applied load during scratching and later measuring the depth of penetration and height of the material pile-up on each side of the scratch or the scratch width. Another preexisting technique to determine the scratch width is direct imaging of the scratch with a microscope or magnifying device. The preexisting methods include many processes and techniques, deterring the widespread use of scratch testing in industrial applications.

Further, with preexisting technology, surface referencing is accomplished by performing an initial scan with a tip at low contact load to map the surface profile. This operation may be carried out prior to, or after the scratch test is performed. In other words, the preexisting methods include two separate operations: scratch formation and surface referencing.

SUMMARY

At least in view of the foregoing, the present inventors have developed an apparatus and method that allows engineers to predict and diagnose the integrity and remaining life of structures utilizing a scratch test.

Provided in one embodiment is a testing apparatus configured to perform scratch experiments to determine mechanical properties of materials. Exemplary applications of this apparatus include in situ field testing of large engineering structures and laboratory testing of small samples, among others.

One embodiment relates to an apparatus. The scratch test apparatus includes an indentor wherein a tip thereof is configured to engage a sample surface, a surface-referencing device configured to establish the position of the indentor relative to the sample surface, a drive mechanism configured to move the indentor along the sample surface to form a scratch, and a measurement device configured to measure at least one of (i) a pile-up height of sample material removed from the scratch and (ii) a width of the scratch.

Another embodiment relates to a method. The method may include creating a scratch in a sample surface with an indentor, and measuring at least one of a pile-up height of sample material removed from the scratch and a scratch width. The creating and measuring may be carried out simultaneously or sequentially by one apparatus.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 18A-C depict various schematic views of an exemplary testing apparatus capable of correcting for a surface curved in the indentor tip travel direction.

FIGS. 20A and 20B depict a schematic perspective view and side view of a surface preparation apparatus, respectively.

DETAILED DESCRIPTION

Following below are more detailed descriptions of various concepts related to, and embodiments of, a scratch testing apparatus and a method of scratch testing. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Provided in one embodiment is a scratch test apparatus configured for the simultaneous formation of a scratch in a material sample with an indentor and the measurement of a scratch depth, scratch width or pile up height of sample material displaced from the scratch. The apparatus may include a surface referencing mechanism that allows the determination of the location of an indentor tip relative to the surface of the material sample.

Instrumented frictional sliding testing, or scratch testing, has recently been proven to allow users to accurately quantify the strength and ductility of metals and other materials including polymers. During a scratch experiment, a hard tip is pressed into a softer material and then ploughs a scratch along its surface. The ploughing of material during the scratch formation induces a steady flow of permanent deformation in the softer material. While a variety of tip shapes are possible, typically a conical tip forms a scratch in the surface of the material having a triangular cross-section with an identifiable depth and width. The material displaced from the scratch is piled on both sides of the scratch on the sample surface, and the piles have an identifiable height relative to the surface of the material. The dimensions of the scratch (e.g., width, depth relative to the surface of the material) and the piles of displaced material (e.g., height relative to the surface of the material), along with the normal reaction force between the tip and the test sample, are used as inputs into reverse algorithms which output the stress versus strain curve for the material.

Figure 1:
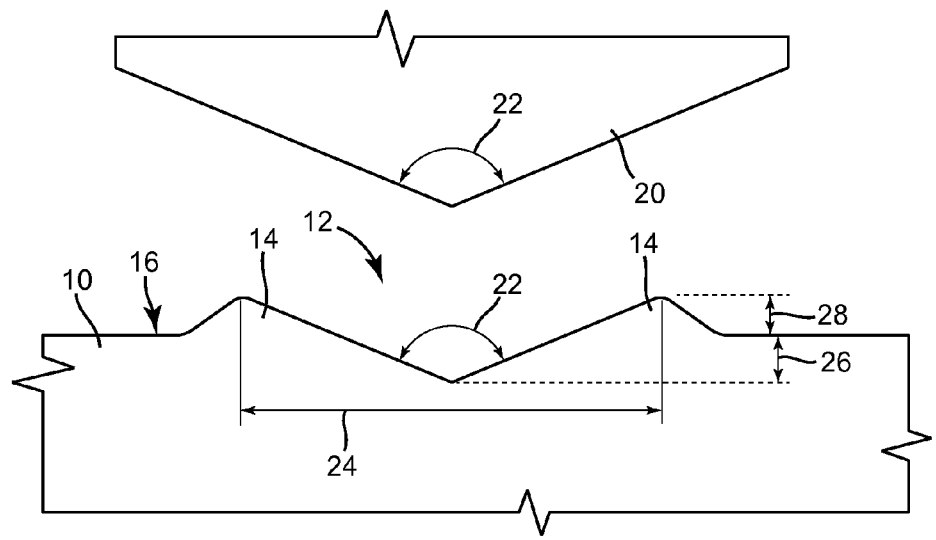
FIG. 1 is a schematic front view of an indentor and a scratch formed in a material sample by the indentor, according to an exemplary embodiment.

An apparatus provided herein is configured to determine mechanical properties of a material sample by performing a scratch test. In at least one embodiment, the apparatus may be also referred to as a testing apparatus, particularly when the apparatus is configured to perform a mechanical test to evaluate mechanical properties of a sample material. Referring to FIG. 1, an indentor 20 is forced into a material sample 10 by moving it in a direction normal to the surface 16 of the material sample 10 and forming a scratch 12 in the material sample 10 by moving the indentor 20 along the surface 16 of the material sample 10. As the scratch 12 is formed in the material sample 10, the displaced material forms piles 14 on both sides of the scratch 12 on the surface of the material sample 10. The amount of material displaced by the indentor 20 may be dependent on the geometry of the indentor (e.g., the indentor angle 22), the normal force applied to the indentor 20, and the physical properties of the material sample 10. The physical properties of the material sample 10 may be determined by analyzing the scratch 12, such as by measuring the scratch width 24, the scratch depth 26, and the pile up height 28 of the scratch.

According to an exemplary embodiment, the indentor 20 includes an indentor tip 54 that has a conical geometry at a total included angle 22 between about 120° and about 160°, which corresponds to about 10° to about 30° of cone surface elevation with respect to the sample surface 16. The angle of the indentor tip 54 may have an effect on the material response during testing, and is selected based on the contact conditions—such as friction. The indentor tip 54 may have other types of geometries (not shown in the figure). For example, the tip may be pyramidal, spherical, or any other suitable geometries. For example, the tip may have any suitable bottom cross-section, such as a triangular cross-sectional. In one example, the indentor 20, or the tip 54 thereof, may be any commercially available indentors (or tips), including Vickers, Rockwell, etc. indentors. The term "indentor" herein need not be necessarily a material used to perform indentation and instead may refer to any material that has a hardness value higher than the material sample (to which the indentor is applied to penetrate to produce and indentation or scratch). The indentor 20 may be formed of any material with a sufficient hardness to penetrate the material sample 10 and form the scratch 12 in the material sample 10, including, but not limited to, silicon, titanium oxide, sapphire, diamond, and steel with an appropriate coating or surface treatment.

The testing apparatus in one embodiment is configured to form a scratch in a material sample with a known normal load or a known scratch depth. When the apparatus is set in a mode involving a predetermined scratch depth, the testing apparatus may control the depth and orientation of the indentor regardless of the surface contours of the material sample. For example, the testing apparatus may maintain the indentor at a predetermined depth below the material surface. The testing apparatus may be configured to continuously measure experimental parameters during the scratch test. In one embodiment, the apparatus provided herein simplifies and expedites the testing procedure in comparison to the preexisting scratch test apparatus. The testing apparatus may determine a full set of mechanical properties of a material sample without damaging the structure of the material as a whole. In addition, the testing apparatus system allows for the measurement of changes in (local) material mechanical properties along the length of a scratch. The testing apparatus may therefore be utilized for material property characterization in advanced small-scale fabrication, as well as in traditional industries involving welded structures, damaged structures, wear applications and other locations that are susceptible to failure.

The testing apparatus therefore may provide a tool for accurately probing for mechanical material properties in manufacturing quality control, condition assessment, and diagnostic testing applications. The testing apparatus may provide a system configured to perform a testing method for evaluating mechanical properties of engineering, or structural, materials, including a measure of the strength, hardness, and ductility. The testing apparatus provides an apparatus and instrumentation to simplify the implementation of the testing method. The testing apparatus may be configured to be portable so that it may be attached to existing large structures, or may be used in small-scale laboratory testing.

Referring now to FIGS. 2-11, a testing apparatus 30 is shown in detail according to several exemplary embodiments. As shown schematically in FIGS. 2 and 3, the testing apparatus 30 includes a support structure 32 to which the indentor 20 is mounted and a surface-referencing device 40 coupled to the support structure 32. The support structure 32 provides alignment and support for the indentor 20. The indentor 20 is moved relative to the surface 16 of the material sample 10 to form a scratch by applying a normal load to the support structure 32 with a load transfer module 34 and applying a transverse load to the support structure 32 with a drive mechanism 36. According to an exemplary embodiment, the drive mechanism 36 is coupled to the support structure 32 with a coupling member 35, shown as a mechanical link. The testing apparatus 30 may be coupled to the material sample 10 with a mounting structure 38. As the scratch 12 in the material sample 10 (on the surface thereof as shown here) is formed by the indentor 20, the testing apparatus 30 simultaneously measures the scratch with a measurement apparatus 39 coupled to the support structure 32. The formation of scratch and measurement need not occur simultaneously. In one embodiment, these two processes may take place sequentially. In one embodiment, regardless of whether the two processes take place simultaneously or sequentially, the two processes are carried out by one single apparatus. In one embodiment, the two processes, sequential or simultaneous, may be carried out by one single drive mechanism. In another embodiment, the two processes, sequential or simultaneous, may be carried out by multiple drive mechanisms of one single apparatus.

Referring to FIGS. 3-8, a tilt correction and surface-referencing device 40 is shown coupled to the support structure 32. The surface-referencing device 40 enables reliable monitoring and/or control of the position of the indentor 20 in a direction normal to the surface 16 of the material sample 10 at the same time that the scratch 12 is being made. As described further below, the surface-referencing device 40 may establish the position of the indentor relative of the sample surface. The establishing of the position in one embodiment may refer to detecting the position, although establishing need not involving detection. The testing apparatus 30 is configured to operate in a monitor mode or a control mode. In one embodiment, whether a mode is monitor or control is designated with respect to the normal force at the indentor tip (or the indentor itself in some instances) during a scratch test. In the monitor mode, the surface-referencing device 40 allows the testing apparatus 30 to establish the depth of penetration of the indentor 20 under a predetermined applied normal force. In the control mode, the surface-referencing device 40 allows the testing apparatus 30 to form a scratch of a constant and known depth, and to detect the reaction force and either the height of material pile-up or width of the scratch. In either the monitor mode or the control mode, the data collected by the surface-referencing device 40 may be utilized with reverse algorithms to predict the stress-strain curve of the material sample 10 and establish a quantitative index for the scratch and indentation hardness, yield strength, ultimate testing strength, strain hardening behavior and elongation at break of the material sample 10.

According to an exemplary embodiment, the surface-referencing device 40 includes a first member 60 disposed over one side of the indentor 20, positioned laterally from the indentor 20 and a second member 60 disposed on the opposite side of the indentor 20 from the first member 60. The first member may be disposed in a direction normal to the direction of the forces applied by the load transfer module 34 and the drive mechanism 36. The profile of the surface 16 may be determined by measuring the elevation on each side of the scratch 12 as it is being formed by the testing apparatus 30. In some instances, the profile may be determined shortly after (e.g., immediately after) the elevation is formed. The surface-referencing device 40 performs a surface referencing operation simultaneously with the formation of the scratch 12.

Figure 3:
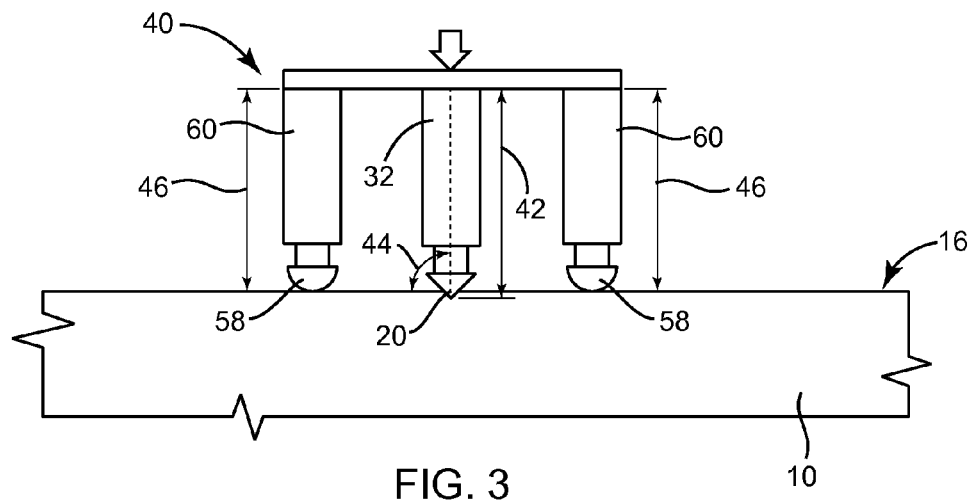
FIG. 3 is a schematic front view of a surface-referencing device for the scratch testing apparatus of FIG. 1.

Referring to FIG. 3, the elevations 46 of the surface referencing members 60 on either side of the indentor 20 are either monitored or controlled during testing. When the testing apparatus 30 is operating in the monitor mode, the sample slope is established by establishing the elevation of the original (undeformed) surface along the trajectory of the indentor 20. These elevations may be monitored using any suitable technology, including contactless sensors based on optics, capacitance, or inductance, and displacement probes such as leaf springs and linear voltage displacement transducers (LVDTs). In one embodiment, when the testing apparatus 30 is operating in control mode, the elevations 46 of the surface referencing members are maintained at the same value, allowing for both the control of the slope of the trajectory of the indentor 20 and lateral tilt-correction of slope 44 perpendicular to the trajectory of the indentor 20. In high load applications, the surface-referencing device 40 may be utilized to allow for rotation and self-alignment of the testing apparatus 30, minimizing (or even eliminating, in some instances) the need for a closed-loop control of measurement and correction of position. High load applications may include applications in which the testing apparatus 30 is sufficiently rigid to transform the contact force between the surface 16 of the material sample 10 and the surface-referencing device 40 into a rotation of the support structure 32. In low load applications where the corrective torque provided by the surface-referencing device 40 to the support structure 32 is insufficient to provide tilt-correction, the surface-referencing device 40 may only provide elevation-correction. Low load applications may include applications in which the contact force between the surface 16 of the material sample 10 and the surface-referencing device 40 is not translated into a rotation of the support structure 32. Tilt-correction may not be needed when the sample and test system are set perpendicular or close to perpendicular—e.g., to within a few degrees of perpendicular, depending on the accuracy needed. The surface referencing using elevations 46 may reference the surface 16 in a direction transverse to the direction of the scratch 12.

Figure 4:
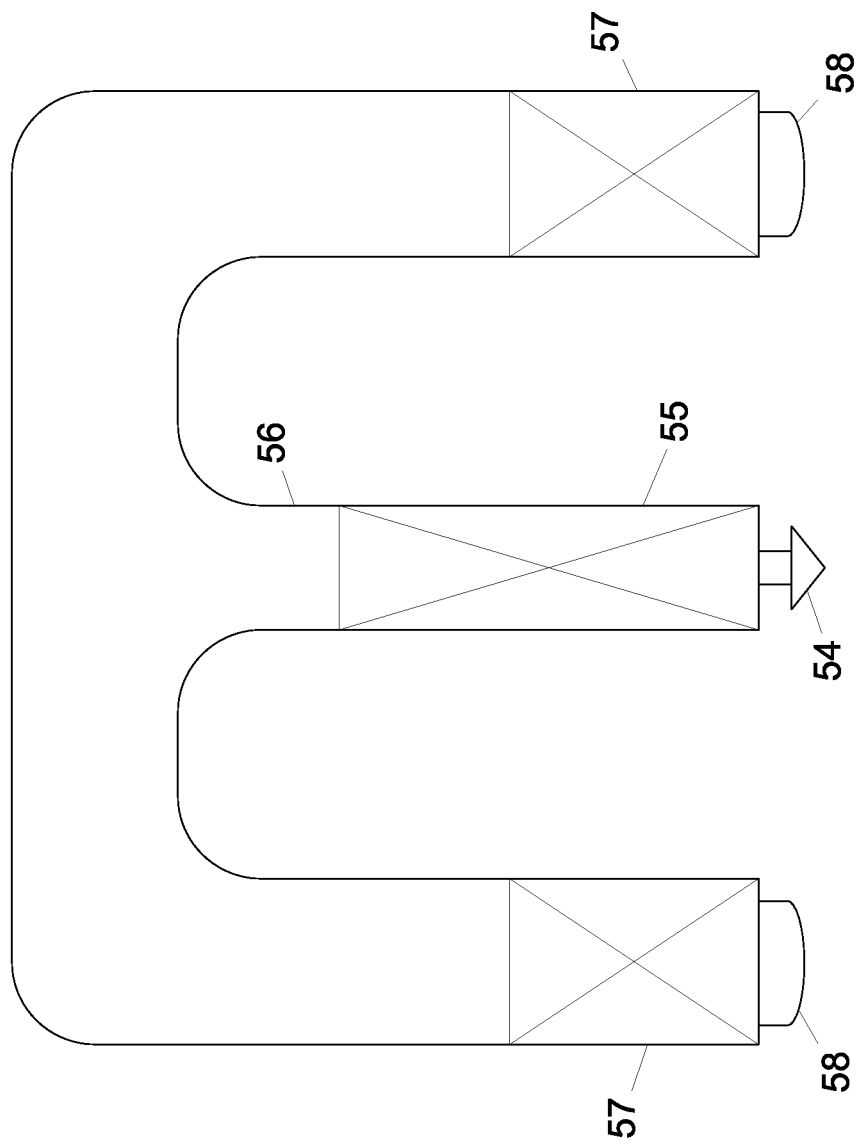
FIG. 4 is a schematic front view of the surface-referencing device of FIG. 3, showing a load indicator and one example a force module (a force probe in this particular instance).

Referring to FIG. 4, a schematic front view of the surface-referencing device 40 is shown in control mode. Lateral tilt correction may be achieved through contact floats 58 provided at the distal ends of members 60 disposed on either side of the indentor 20. According to an exemplary embodiment, the indentor 20 may include an indentor tip 54 that is coupled to an indentor tip column 56. The normal reaction force at the indentor 20 between the tip 54 and the sample surface 16 may be measured during the scratch test. The testing apparatus may include a force module, with the force module being either a force probe or a normal load application mechanism. The value of the normal reaction force at the indentor 20 may be determined, for example, by a force probe 55 in either the control mode or the monitor mode. The force probe 55 may be employed to measure any applicable force (or load), including a normal force. A normal load application mechanism, as described further below, may comprise, for example, an actuator, including, for example, a linear actuator.

The floats 58 may include electrical contact indicators or contact load indicators 57 such that an error message may be provided if contact between the floats 58 and the surface 16 of the material sample 10 is lost. The floats 58 may establish contact with the sample surface 16 through frictional sliding, rolling contact, air flow or other flotation mechanism. The contact between the floats 58 and the sample surface 16 may be elastic, although in some instances plastic contact may be possible. The floats 58 may be adjustable to allow for a change in the scratch depth. For example, in one embodiment, the floats 58 may be movable relative to static members 60 that are fixed to the support structure 32. The floats may be movable in a direction normal to the sample surface 16. Other directions of movement are also possible. In another embodiment, the entire surface-referencing device 40 may be movable relative to the support structure 32. In still another embodiment, a variety of testing apparatuses 30 may be provided, each testing apparatus having a different relative height between the floats 58 and the indentor 20.

In another embodiment, when in monitor mode, the testing apparatus 30 is configured to perform a load-controlled mechanical test. The normal reaction force between the tip 54 and the sample surface 16 is controlled by applying a predetermined force through the tip column 56 or the indentor tip 54 itself. The set force may be applied, for example, by adjusting the height of the surface-referencing device 40, as described above. In this case, a normal load application mechanism of a force module may transfer a constant load (or "force") applied from the tip column 56 to the indentor tip 54, and monitor the applied load. In one embodiment, the tip 54 may be rigidly mounted to the tip column 56, as shown in FIG. 4. In another embodiment, the tip 54 may be movable relative to the tip column 56. For example, the tip 54 may be mounted to a movable piston actuated by any appropriate method, including electromechanically, mechanically, hydraulically, pneumatically, etc. In other embodiments, the tip 54 may be movable relative to the tip column 56 by another mechanism, such as with a threaded connection.

In one embodiment, when in control mode, the testing apparatus is configured to perform a displacement-controlled test. If the tip 54 is rigidly fixed to the tip column 56, the normal reaction force is measured. In the control mode, the depth of the scratch is controlled. The force probe 55 may constantly measure the reaction force (e.g., normal reaction force) on the indentor tip 54. The force probe 55 may measure the normal force by a variety of direct, or indirect, methods. In one embodiment, the normal reaction force is detected by monitoring the deformation of the indentor 20, such as with a strain gauge detecting the strain on the surface of the tip column 56 or other component of the vertical assembly, or by monitoring the change in height of all or a portion of the tip column 56—e.g., with an optical sensor, such as a laser sensor, an inductance sensor, etc. In another embodiment, the normal reaction force is detected with an in-line force transducer mounted within the tip column 56.

Figure 5:
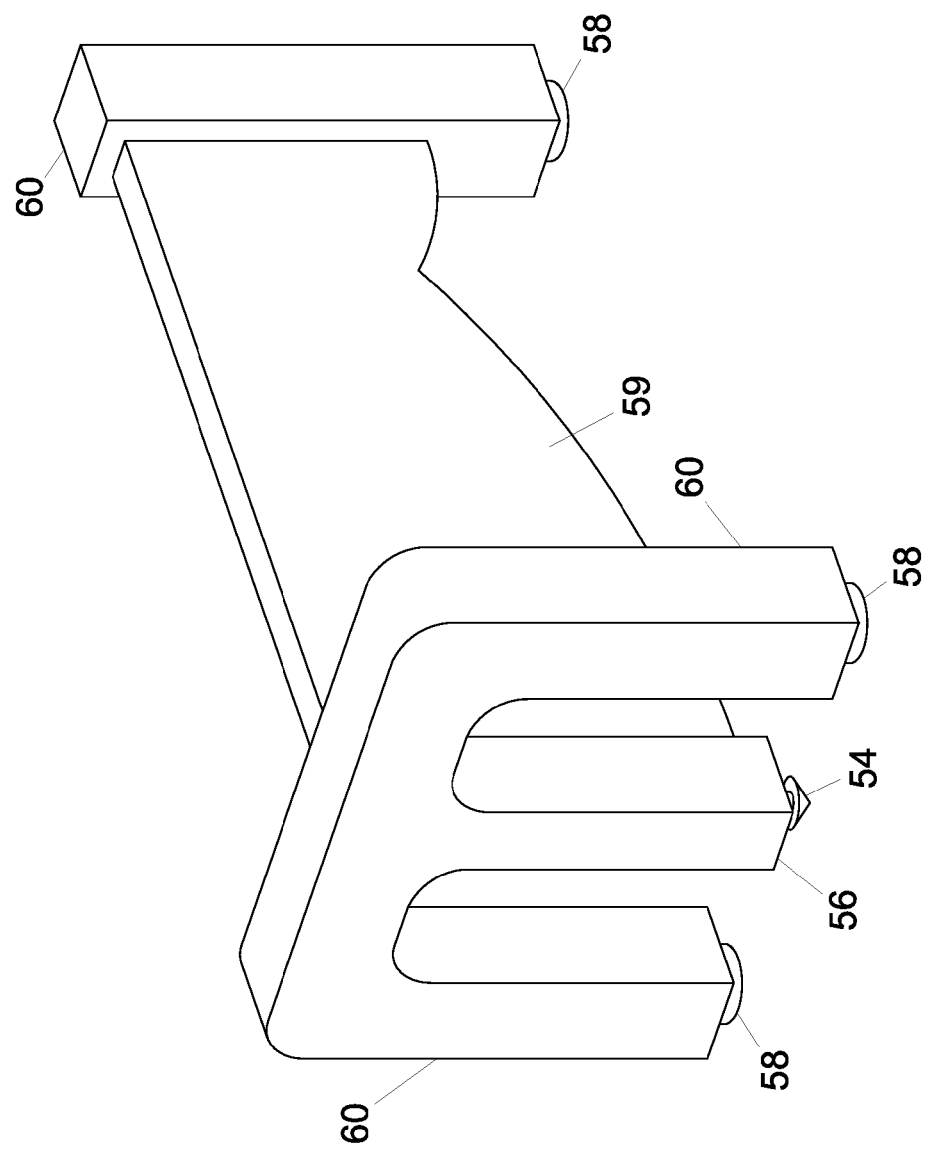
FIG. 5 is a schematic perspective view of an exemplary surface-referencing device for the scratch testing apparatus of FIG. 1.
Figure 6:
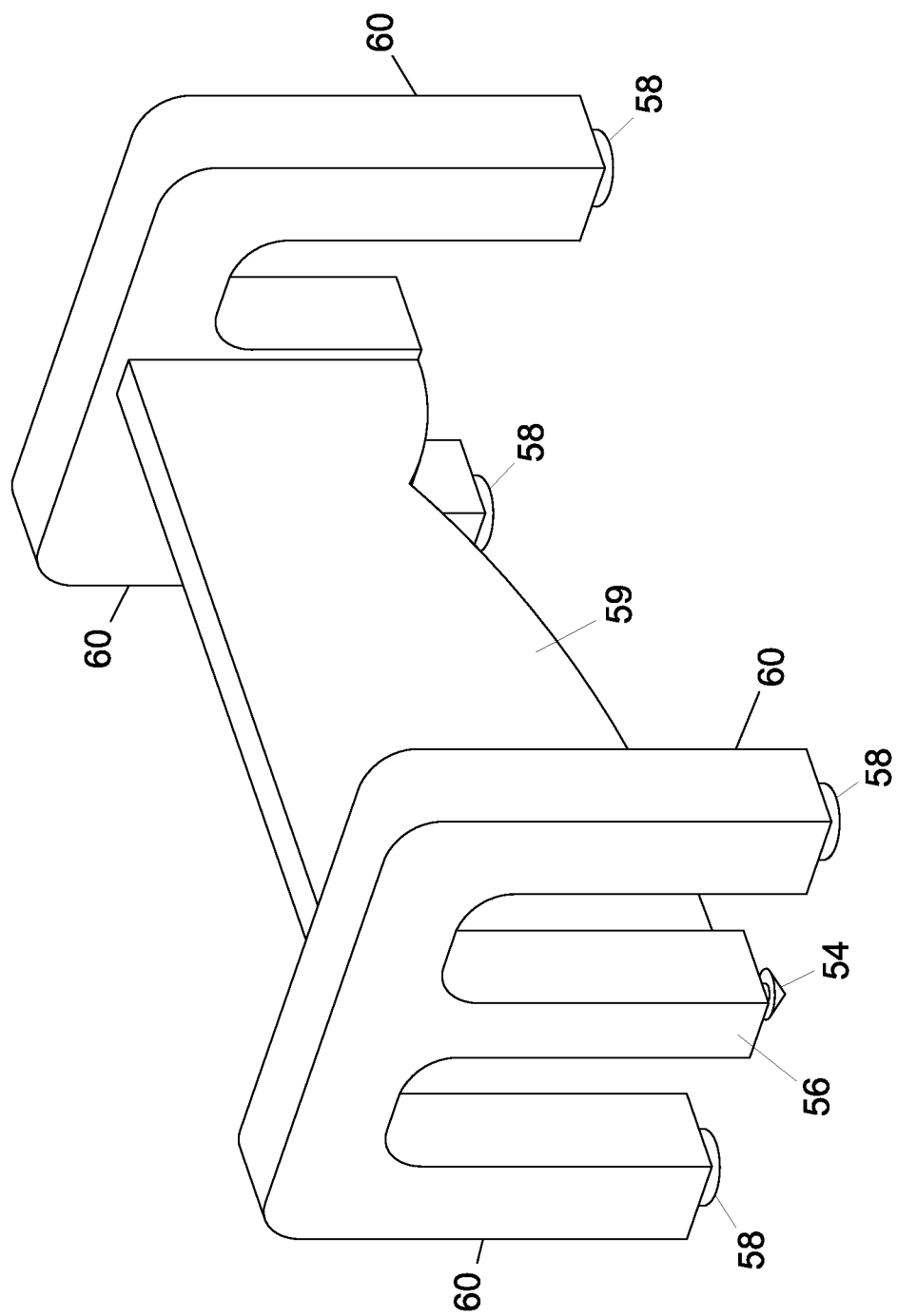
FIG. 6 is a schematic perspective view of another exemplary surface-referencing device for the scratch testing apparatus of FIG. 1.

Referring to FIGS. 5-6, the surface-referencing device 40 may additionally include members 60 including contact floats 58 positioned rearward from the indentor 20—e.g., in a direction opposite of the trajectory of the indentor 20 and the direction of the scratch. In one embodiment, the surface-referencing device 40 may include a single member 60 positioned in line with the trajectory of the indentor 20 as shown in FIG. 5. In another embodiment, the surface-referencing device 40 may include two or more members 60 positioned rearward from the indentor 20 as shown in FIG. 6. The members 60 may be in line with the trajectory of the indentor 20, or may be positioned laterally, to the side of the trajectory of the indentor 20. The rearward members and the members positioned on either side of the indentor 20 may be utilized to reference the sample surface 16 in the direction of the trajectory of the indentor 20.

Figure 7:
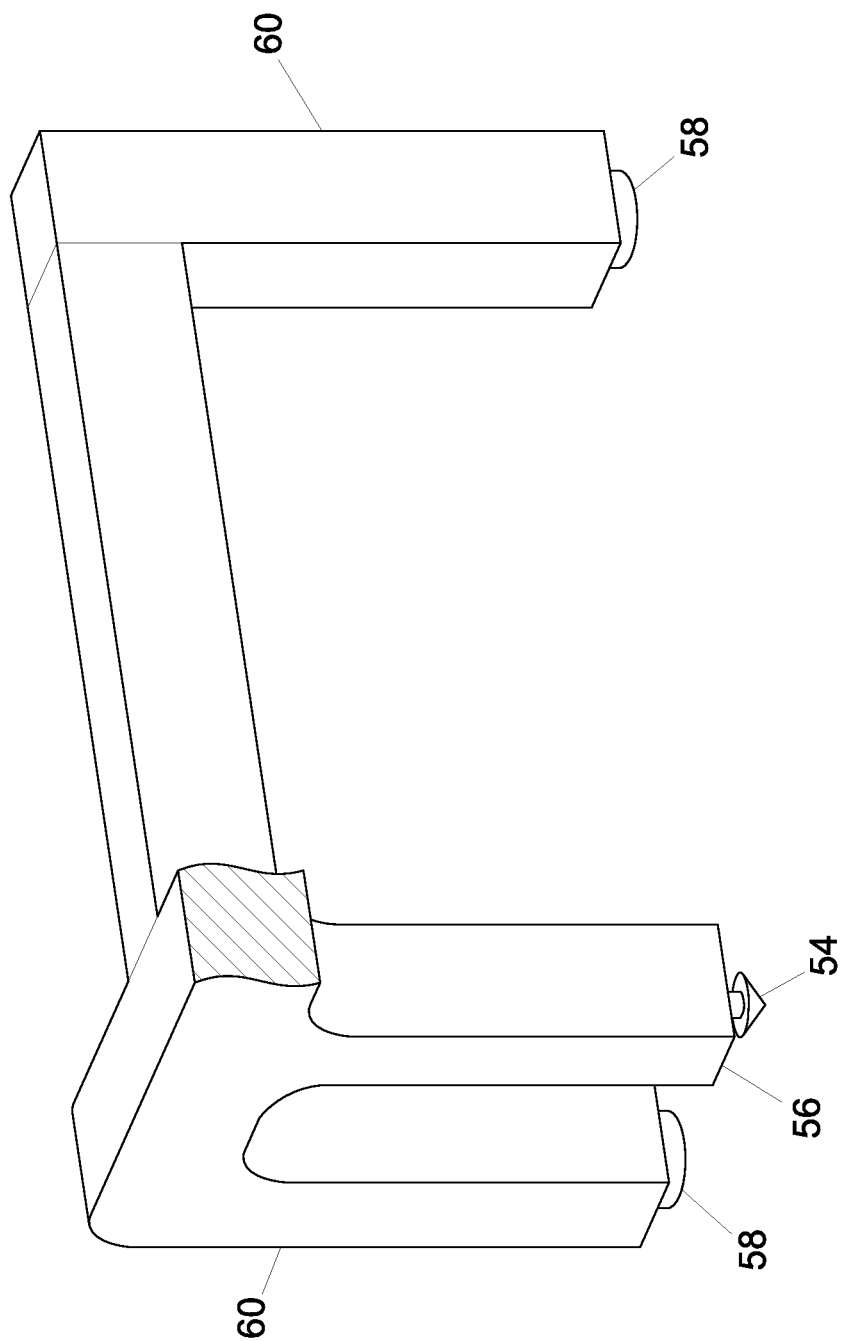
FIG. 7 is a schematic perspective view of another exemplary surface-referencing device for the scratch testing apparatus of FIG. 1.
Figure 8:
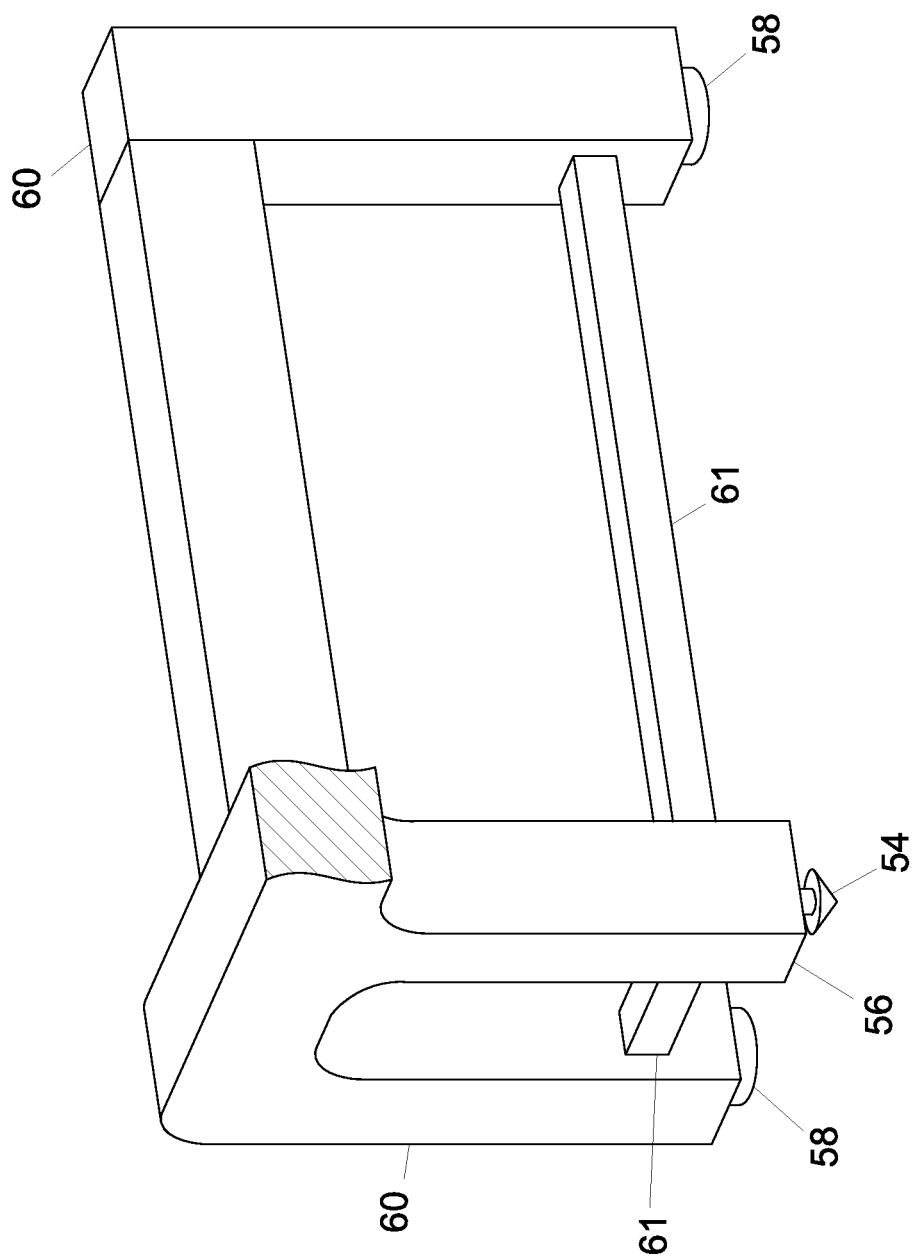
FIG. 8 is a schematic perspective view of another exemplary surface-referencing device for the scratch testing apparatus of FIG. 1.

Referring to FIGS. 5-8, the support structure 32 may be configured to provide lateral support to isolate the lateral frictional load from the normal reaction force on the tip column 56. In one exemplary embodiment, as shown in FIGS. 5 and 6, the support structure 32 may include a rib 59 extending parallel to the trajectory of the indentor 20 and the direction of the scratch. The rib may be a plate, gusset, or other reinforcement. In another embodiment, as shown in FIG. 7, the tip column 56 may be configured to have an enhanced stiffness per weight—such as by altering the cross-sectional shape of the tip column. In another embodiment, as shown in FIG. 8, the support structure 32 may include a brace 61, extending between the indentor 20 and the support structure 32.

Figure 9:
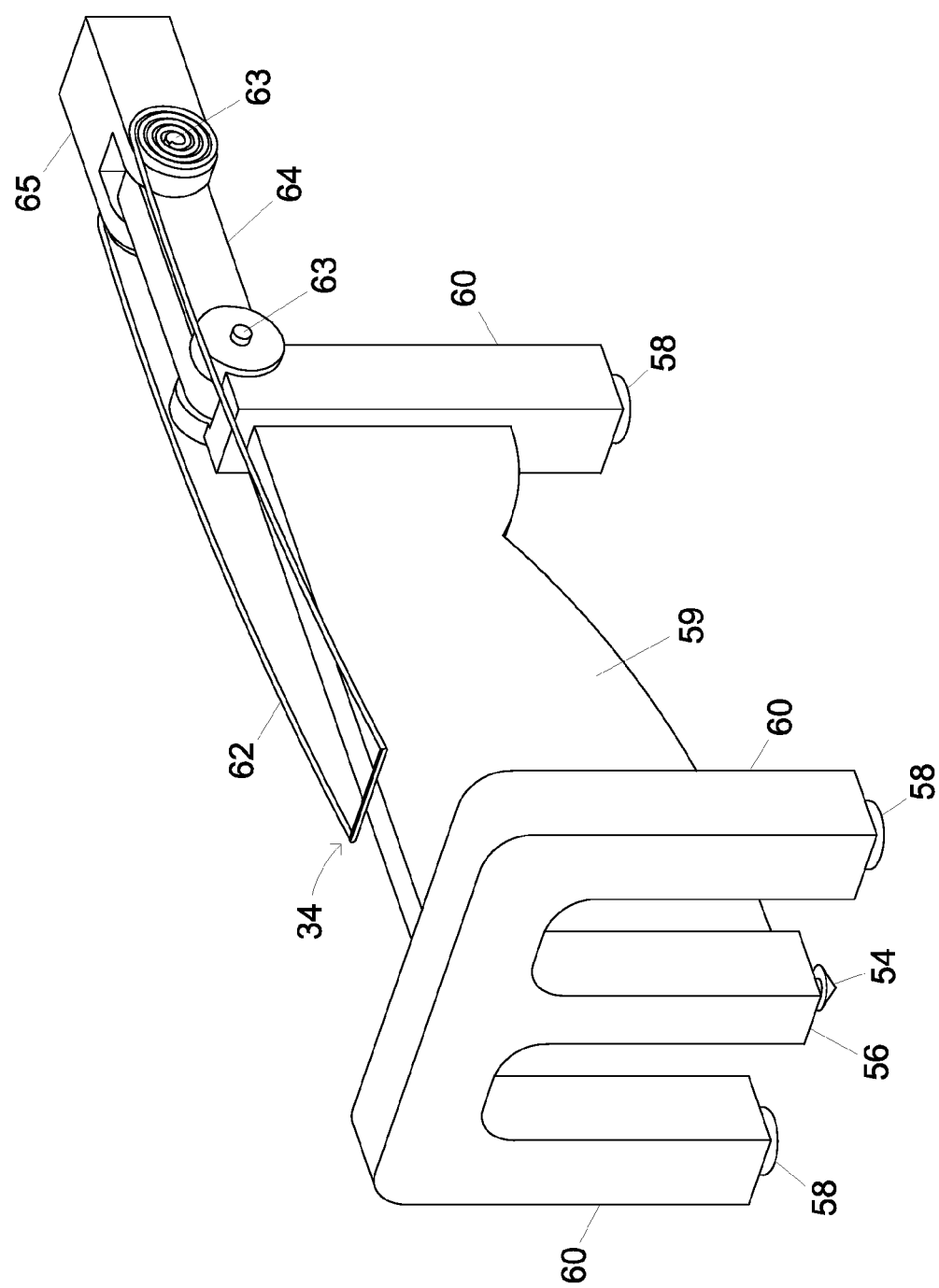
FIG. 9 is a schematic perspective view of an exemplary load transfer module for the scratch testing apparatus of FIG. 1.
Figure 10:
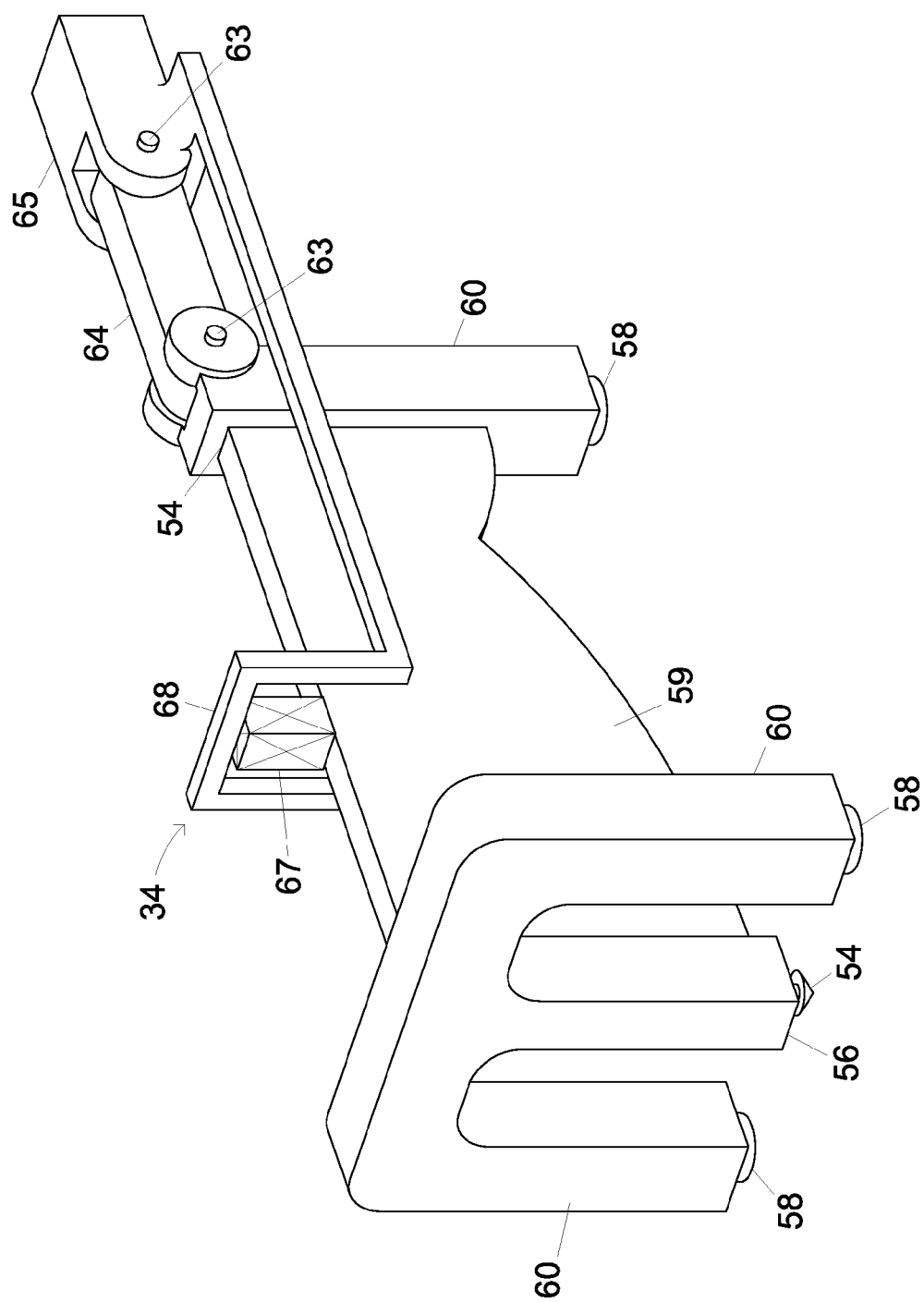
FIG. 10 is a schematic perspective view of an exemplary load transfer module for the scratch testing apparatus of FIG. 1.
Figure 11:
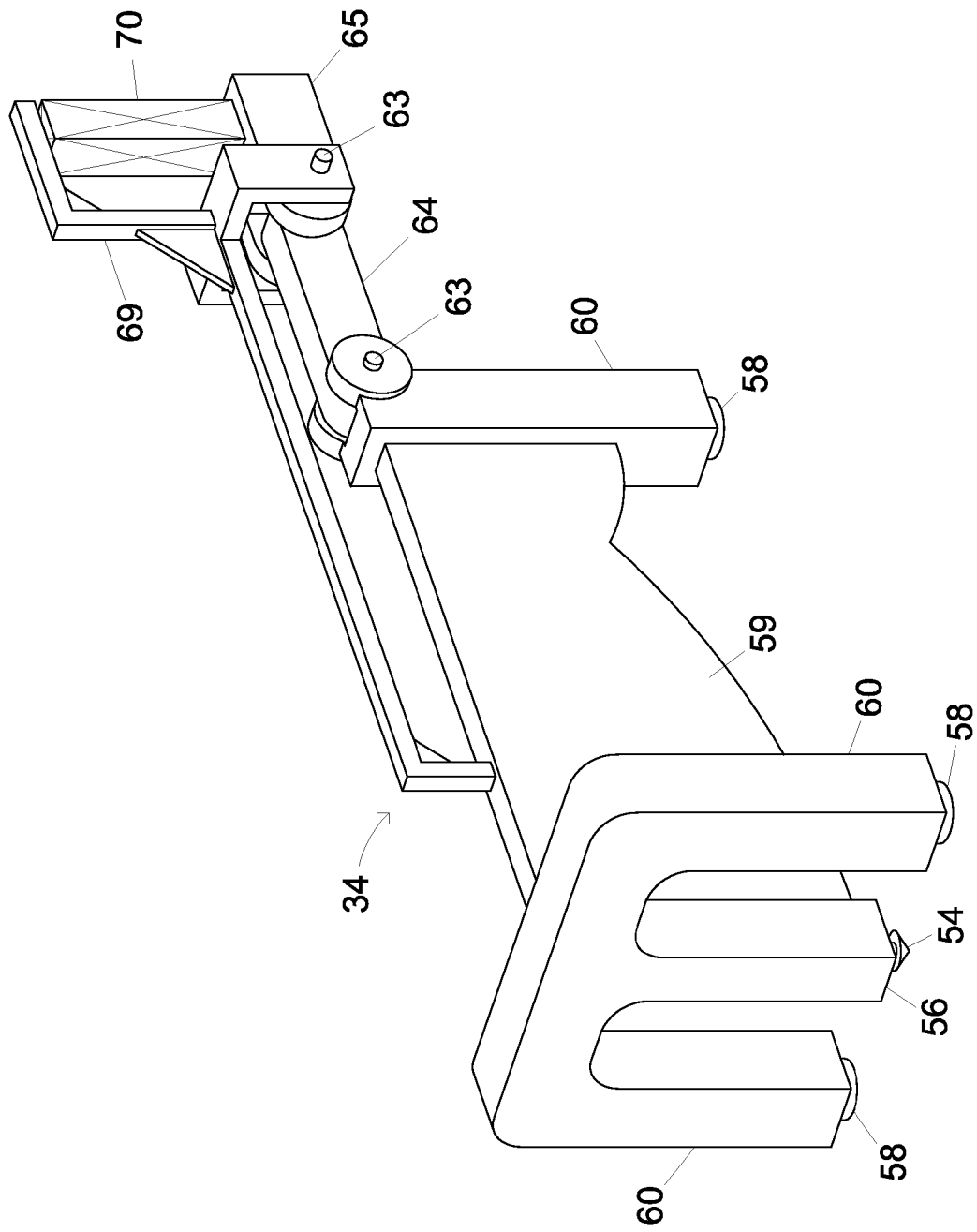
FIG. 11 is a schematic perspective view of an exemplary load transfer module for the scratch testing apparatus of FIG. 1.

Referring now to FIGS. 9-11, the load transfer module 34 applies a normal load to the support structure 32. The normal load is applied to the support structure 32 such that the normal load at the indentor 20 is greater than the reaction force between the tip 54 and sample surface 16. The magnitude of the reaction force is dependent on the sample material 10 being scratched, the geometry of the tip 54, and the depth of the scratch 12. The load transfer module 34 may be any suitable mechanism that applies a sufficient normal load to the indentor 20. The load transfer module 34 may apply a normal load to the indentor 20 through the support structure 32. As shown in FIG. 9, in one embodiment, the load transfer module 34 includes a torsional spring 62. The torsional spring is anchored to a structure fixed to material sample 10, such as the drive mechanism 36, and engages an arm applying a normal force to a portion of the support structure 32, such as the rib 59. In another embodiment, the load transfer module 34 may include another mechanism, such as a linear actuator. As shown in FIG. 10, the load transfer module 34 may include a linear actuator 67 mounted to a support structure 68 anchored to the drive mechanism 36 and applying a normal force to a portion of the support structure 32, such as the rib 59. As shown in FIG. 11, the load transfer module 34 in another embodiment may include a linear actuator 70 mounted to a support structure 69 anchored to the support structure 32 and applying a normal force to the support structure 32 through a transfer arm.

According to an exemplary embodiment, the testing apparatus 30 is configured such that the drive mechanism 36 may transmit translational motion to the support structure 32 and the indentor 20 while the support structure 32 and the indentor 20 may move independently of the drive mechanism 36 in a direction normal to the sample surface 16. The support structure 32 may be coupled to the drive mechanism 36 with a coupling member 35. In one embodiment, the coupling member 35 includes a link 64, coupled to the support structure 32 and to the drive mechanism 36 with pinned connections 63.

Referring to FIGS. 12A-13B, the drive mechanism 36 for providing translational motion along the sample surface 16 is shown according to several exemplary embodiments. The drive mechanism 36 provides translational motion through the link 64 coupled to a transfer head 65 without interfering with the alignment of the indentor 20 as prescribed by the surface-referencing device 40. In other embodiments, the drive mechanism 36 may be coupled to the support structure 32 with another suitable connection. The translational motion may be applied with a lateral force in the pushing or pulling force (e.g., a force in a direction towards or away from the indentor 20). According to an exemplary embodiment, the lateral force is applied with a linear actuator 66 operating in the direction parallel to the sample surface 16 being scratched. The linear actuator 66 may be any suitable mechanism (e.g., mechanical, hydraulic, pneumatic, electromagnetic, etc.) capable of providing a sufficient force to overcome the friction resulting from the normal force applied by the load transfer module 34.

Figure 12A:
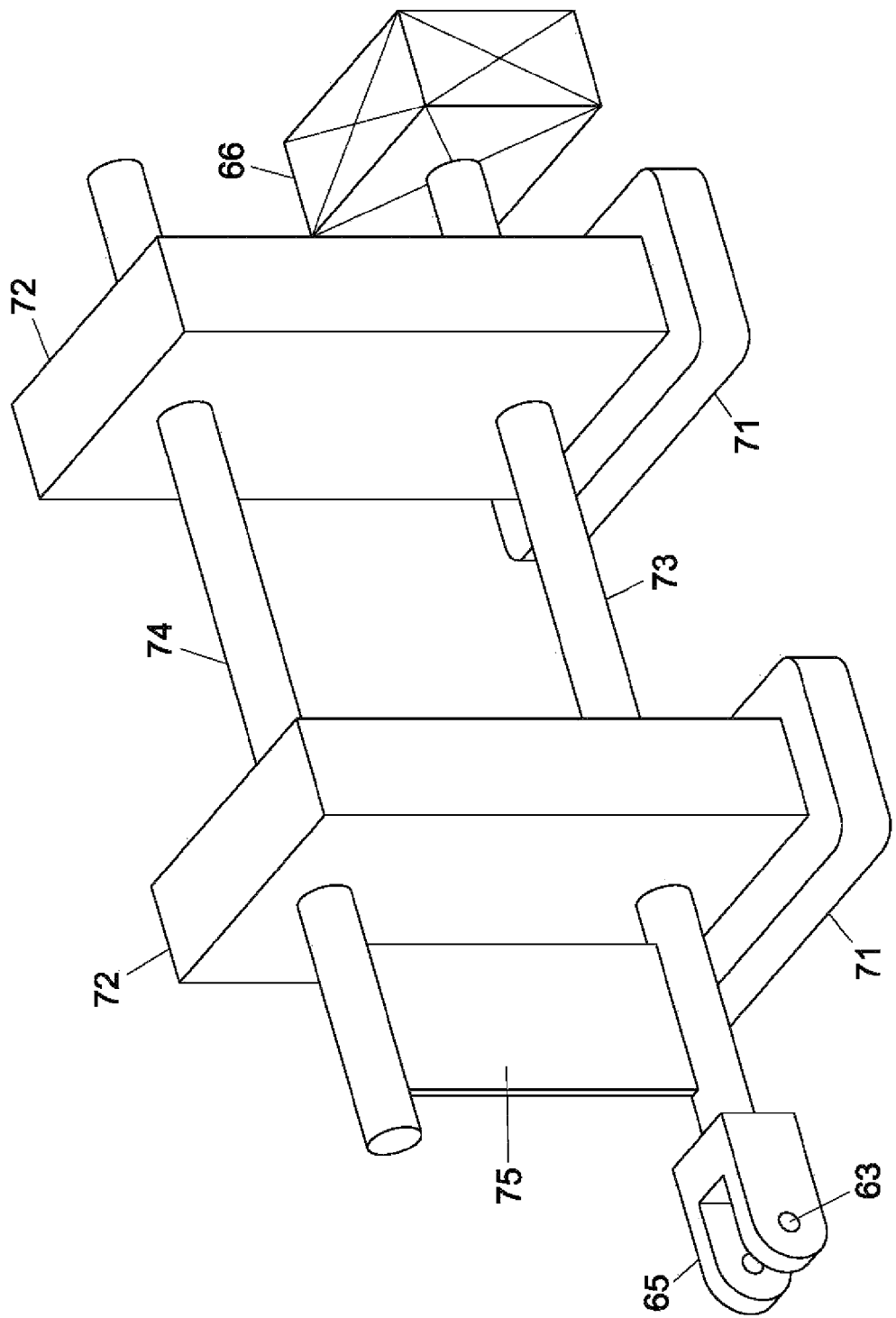
FIG. 12A is a schematic perspective view of an exemplary drive mechanism for the scratch testing apparatus of FIG. 1.
Figure 12B:
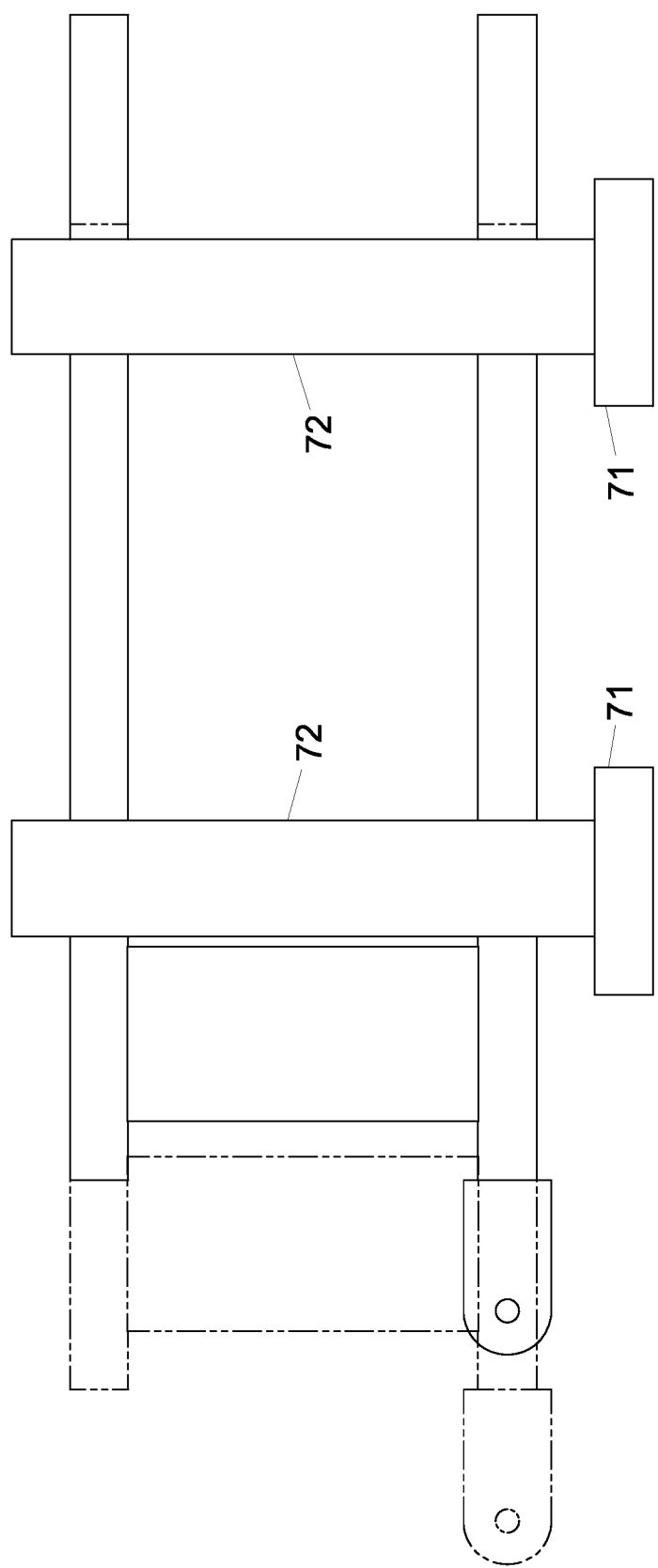
FIG. 12B is a schematic side view of the drive mechanism of FIG. 12A.

Referring to FIGS. 12A and 12B, the linear actuator 66 acts upon a drive pin 73. The drive pin 73 is held in place using a support 72, which may also act to align the drive pin 73 with the desired load application point—e.g., the transfer head 65. The load application point connecting the drive mechanism 36 to the support structure 32 is preferably positioned close to the sample surface 16 to reduce the moment imparted on the indentor 20 when a pushing force is applied and to reduce the tendency to reduce the load applied to the indentor 20 when a pulling force is applied. To provide stability in the drive system, a plurality of supports 72 may be used at multiple locations along the drive pin 73 path to guide an optional secondary drive pin 74 connected to the drive pin 73 by a connecting member 75. Each of the supports 72 may be coupled to the material sample 10 with the mounting structure 38.

Figure 13A:
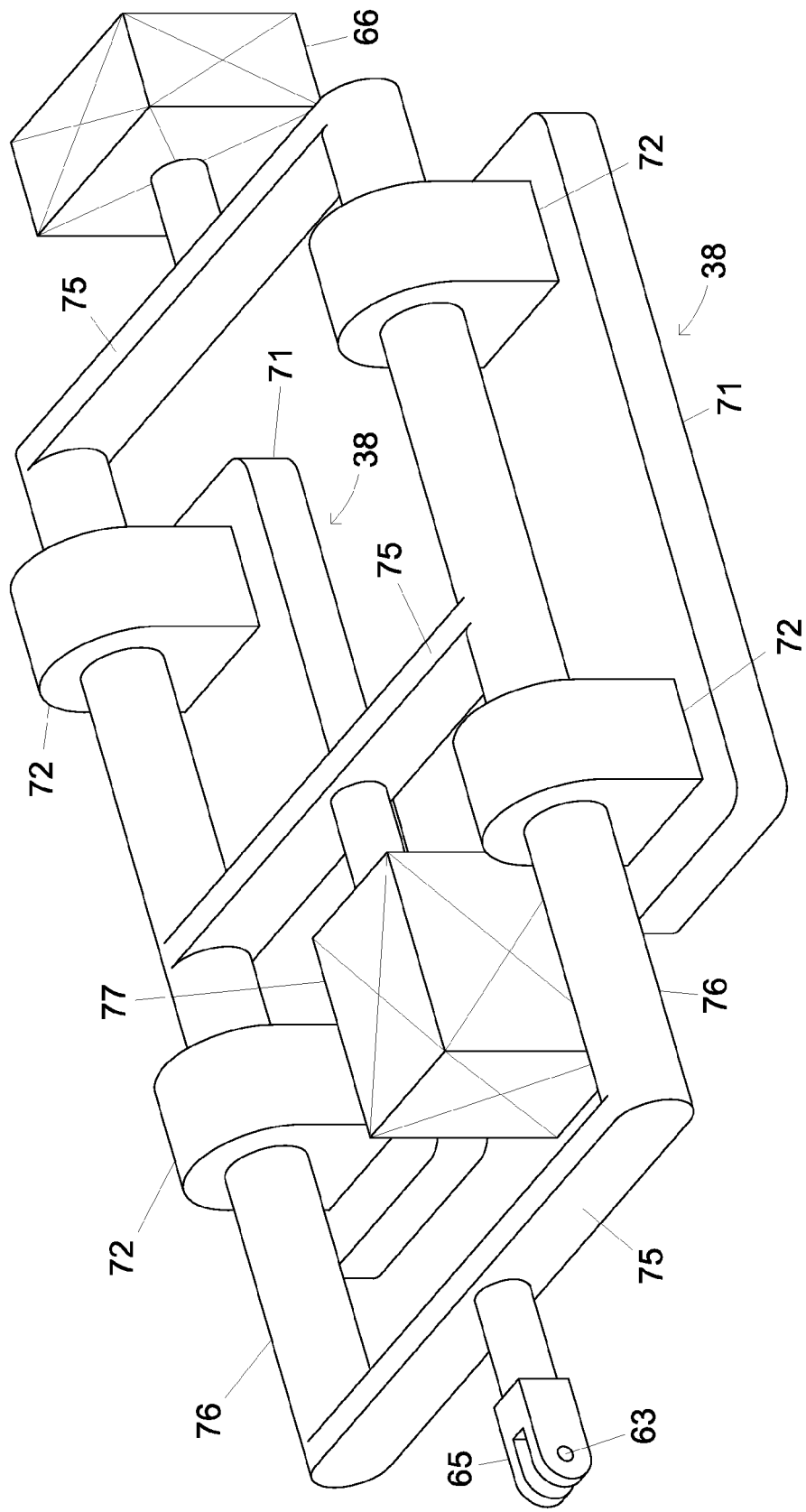
FIG. 13A is a schematic perspective view of an exemplary drive mechanism for the scratch testing apparatus of FIG. 1.
Figure 13B:
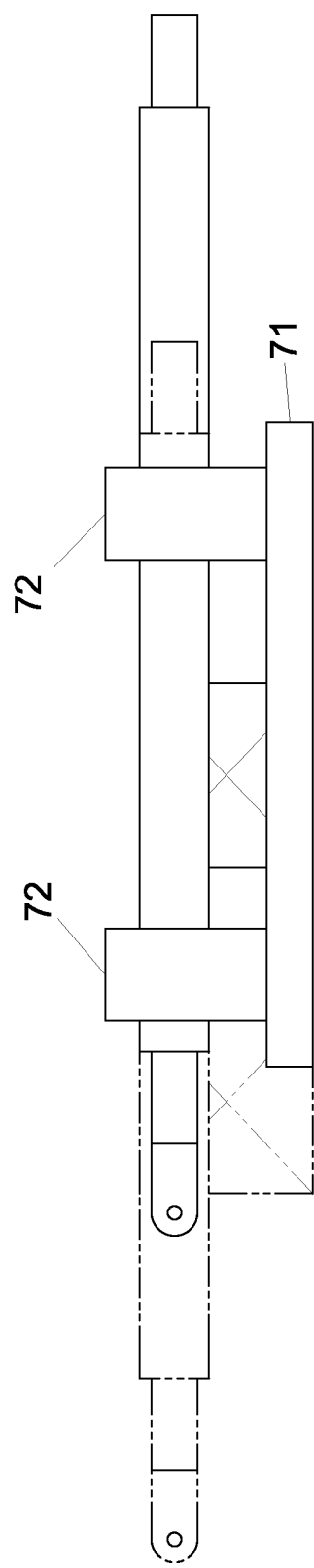
FIG. 13B is a schematic side view of the drive mechanism of FIG. 13A.

Referring to FIGS. 13A and 13B, in another embodiment, the drive mechanism 36 may include multiple drive pins 76. The drive pins 76 are held in place using multiple supports 72, which also act to align each of the drive pins 76. The multiple drive pins 76 may be connected by connecting members 75 such that they act in unison to act upon the desired load application point.

The mounting structure 38 is configured to couple the testing apparatus 30 to the material sample. In the various configurations, each point of fixed contact with the material sample 10—e.g., each one of multiple supports 72, may correspond to a fixed attachment, for a mounting structure 38 where the material sample 10 is mounted to the testing apparatus 30—e.g., a stationary testing apparatus, or may correspond to a fixed point of contact between the material sample 10 and the testing apparatus—e.g., for a portable testing apparatus. In one exemplary embodiment, for a portable testing apparatus, the mounting structure 38 may include magnetic devices similar to those utilized in mag-drills to create the contact, as well as high pressure suction with a ferro-magnetic material sample. In some exemplary embodiments, the testing apparatus 30 may be utilized as a field unit, and the material sample may be prepared—e.g., with a surface preparation, prior to a scratch testing.

Figure 2:
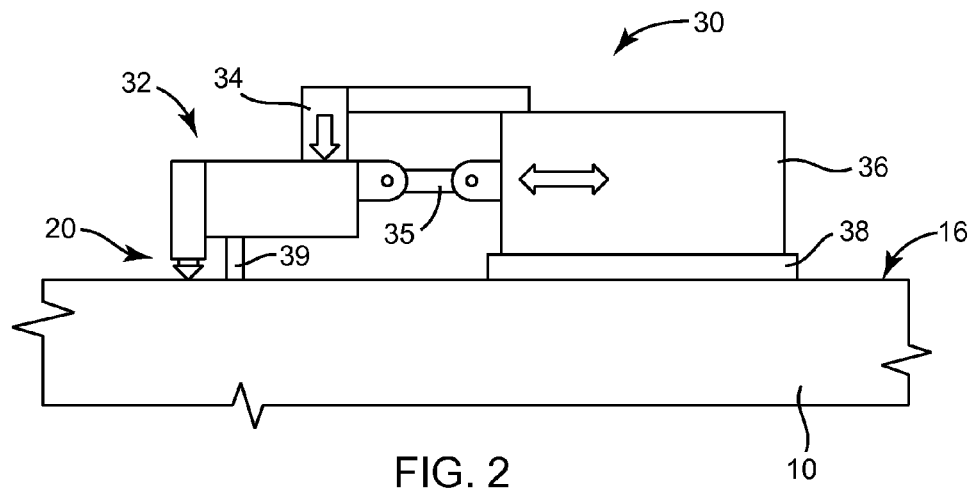
FIG. 2 is a schematic side view of a scratch testing apparatus, according to an exemplary embodiment.

In one embodiment, during the operation of the testing apparatus 30, as described in various embodiments herein, the depth 26 of the scratch 12 is known through the surface-referencing device 40, and the reaction force on the tip 54 of the indentor 20 is either controlled or measured during the operation. The measurement apparatus 39 is configured to detect additional parameters, such as the width 24 of the scratch profile or the pile-up height 28. Computer algorithms may be used to predict the physical properties of the material sample 10 using the scratch depth 26, the reaction force, and at least one of the scratch width 24 and the pile up height 28. As shown in FIG. 2, the measurement apparatus 39 may be positioned behind the indentor 20—e.g., several scratch widths behind the indentor tip 54. In other embodiments, the measurement apparatus 39 may be positioned under the tip column 56 of the indentor 20, or be coupled to one of the trailing floats 58 of the surface-referencing device 40.

The pile-up height 28 may be measured directly using at least one of an optical, electro-magnetic, and mechanical methods. Other suitable methods are possible. The pile-up height 28 may be measured with a contact mechanism or a non-contact mechanism. By detecting the pile-up height with a contact mechanism, the average of the pile-up heights 28 from each side of the scratch 12 may be measured to simplify post-processing methods.

Figure 14:
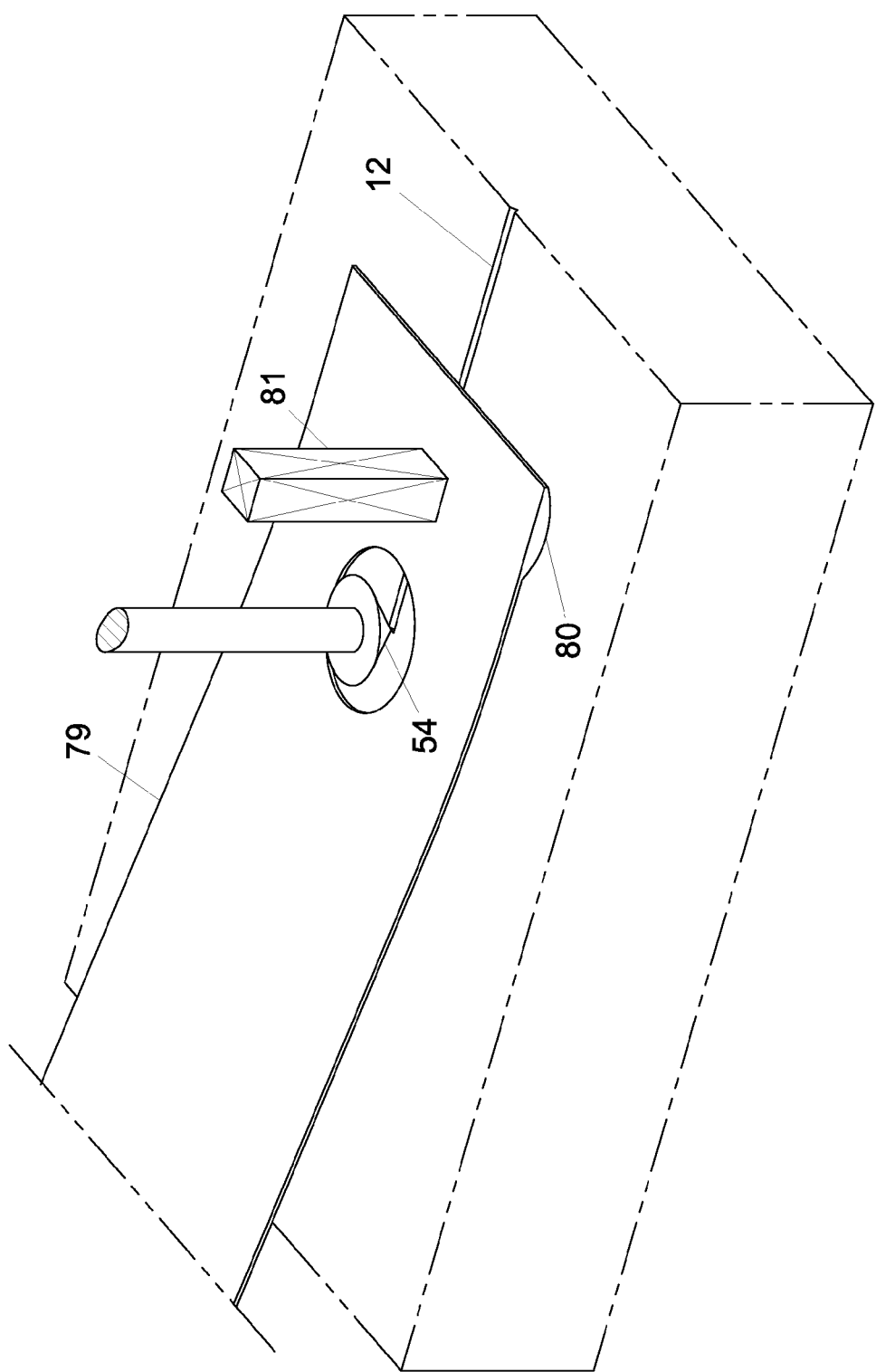
FIG. 14 is a schematic perspective view of an exemplary measurement apparatus for the scratch testing apparatus of FIG. 1.

Referring to FIG. 14, according to one exemplary embodiment, the measurement apparatus 39 may include a leaf spring 79. The leaf spring 79 is mounted to the support structure 32 such that the distal end of the leaf spring 79 is positioned at or below the elevation of the tip 54 of the indentor 20. A protrusion 80—e.g., a wedge or ridge, is provided at the distal end of the leaf spring 79. The protrusion 80 is configured to contact the top of the piles 14 on either side of the scratch 12. The biasing properties of the leaf spring 79 may allow maintaining contact between the protrusion 80 and the piles 14. The contact between the piles 14 and the protrusion 80 deflects the distal end of the leaf spring 79 upward. The magnitude of the deflection of the leaf spring 79 may be detected with a displacement transducer 81 located over the wedge and used to calculate the pile-up height 28. The transducer 81 may be a linear variable differential transformer (LVDT), a plate capacitor, a piezo-electric unit, a laser sensor, an optical focus sensor, or any other suitable device.

Figure 15:
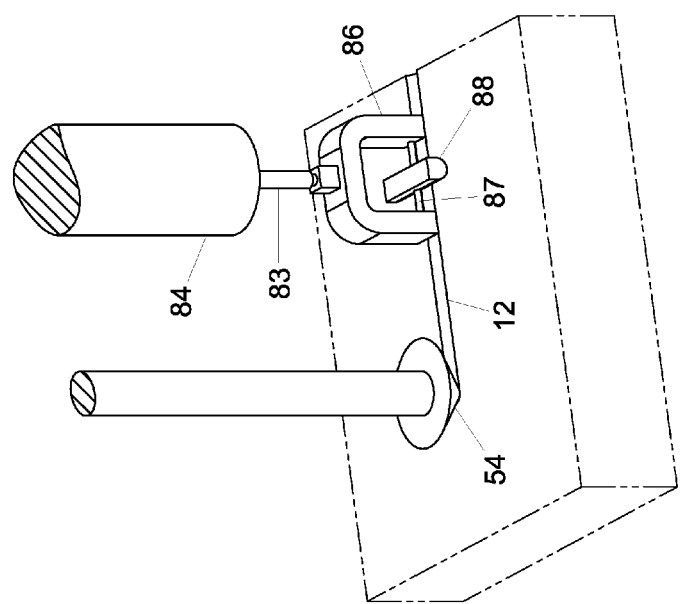
FIG. 15 is a schematic perspective view of an exemplary measurement apparatus for the scratch testing apparatus of FIG. 1.

Referring to FIG. 15, according to another exemplary embodiment, the measurement apparatus 39 may include a linear mechanical displacement transducer 84 mounted to the support structure 32 in a generally vertical orientation. A mount 86 is disposed below the transducer 84 proximate to the sample surface 16 and is coupled to the transducer 84 via a connection rod 83. A wedge beam 88 is coupled to the mount 86 on a freely rotating pin 87, with the pin being oriented generally in line with the trajectory of the indentor 20 and the wedge beam 88 being transverse to the trajectory of the indentor 20 and extending across the width of the scratch 12 such that it contacts the piles 14 on either side of the scratch 12. The magnitude of the deflection of the mount 86 may be detected with the transducer 84 and used to calculate the pile-up height 28. The transducer 84 may be a linear variable differential transformer (LVDT), a plate capacitor, a piezoelectric unit, a laser sensor, an optical focus sensor, or any other suitable device.

In another embodiment, the measurement apparatus 39 may instead be configured to measure the scratch width 24. The scratch width 24 may be measured with profilometry. In one embodiment, the scratch width 24 may be determined by direct imaging with a microscope or magnifying device.

Figure 16:
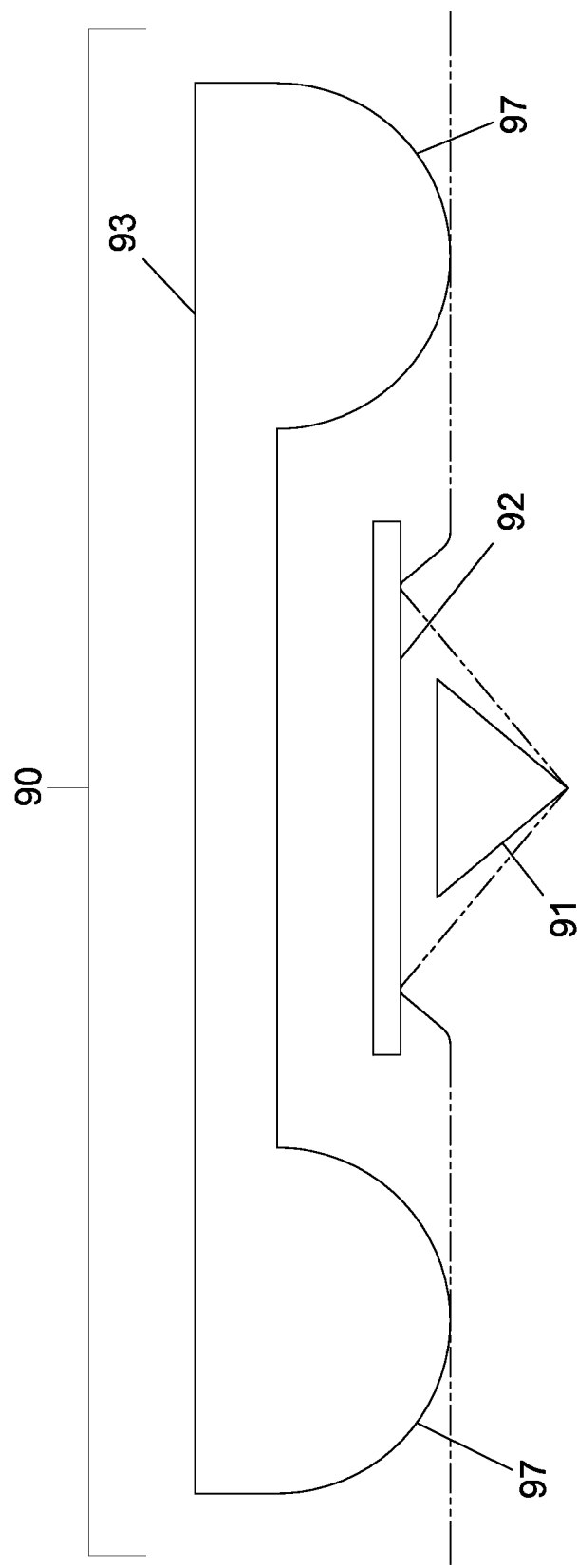
FIG. 16 is a schematic cross-sectional view of an exemplary profile monitoring apparatus that monitors more than one scratch profile feature.
Figure 17A:
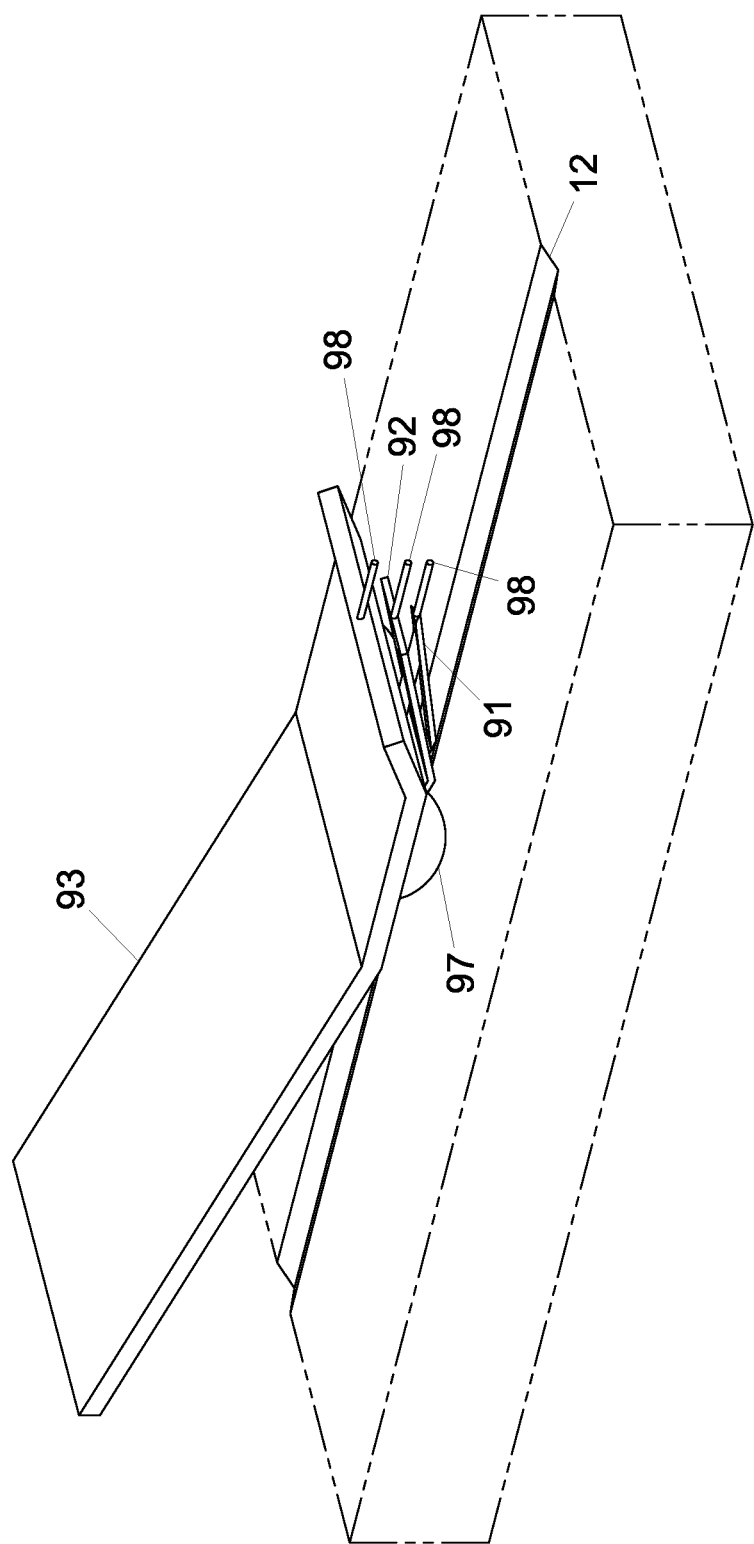
FIGS. 17A-D depict various schematic views of exemplary profile monitoring apparatuses configured to measure scratch profile features.
Figure 17B:
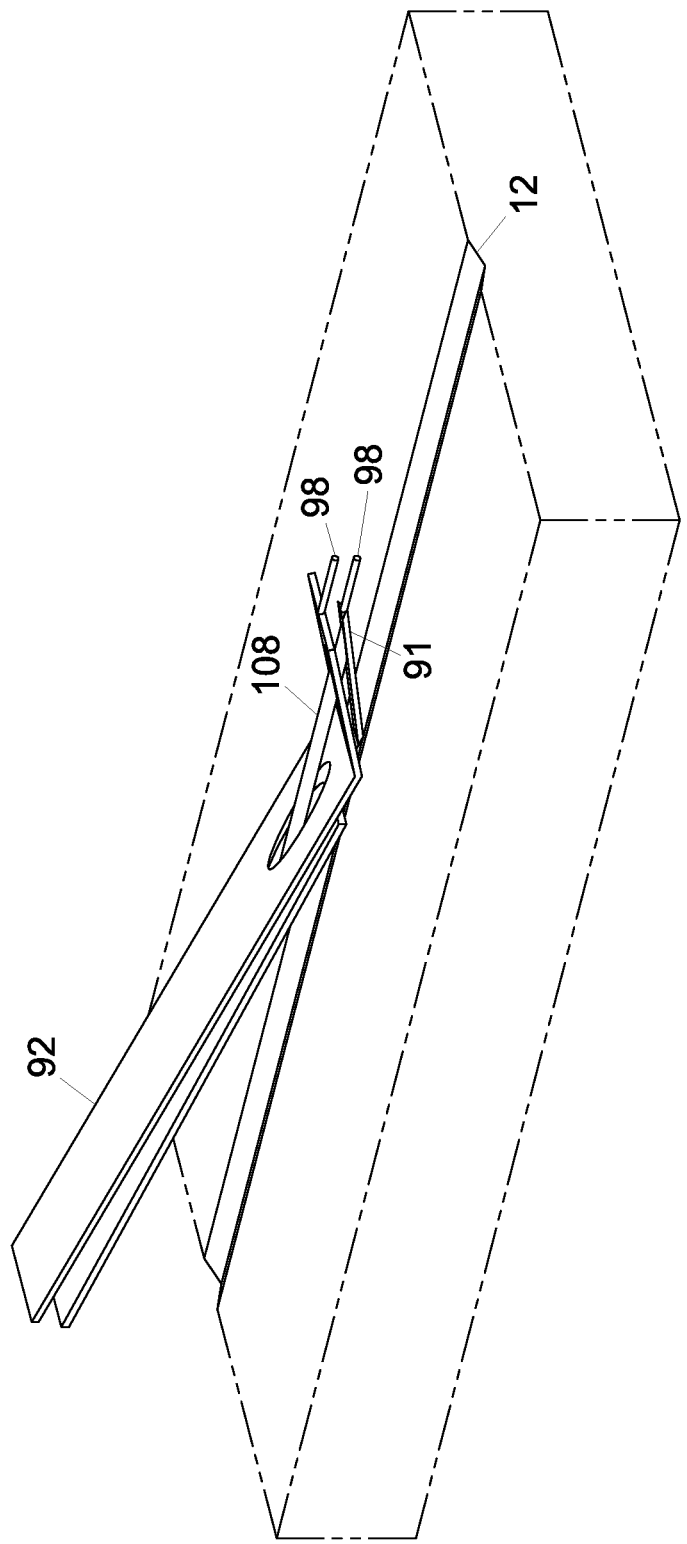
Figure 17C:
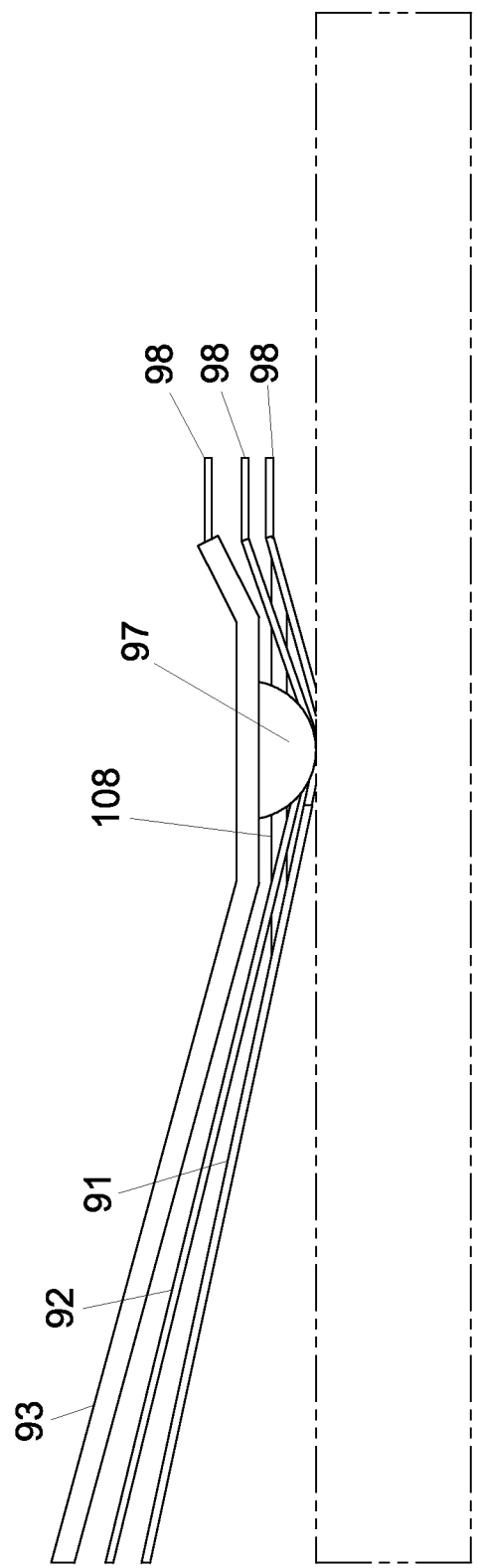
Figure 17D:
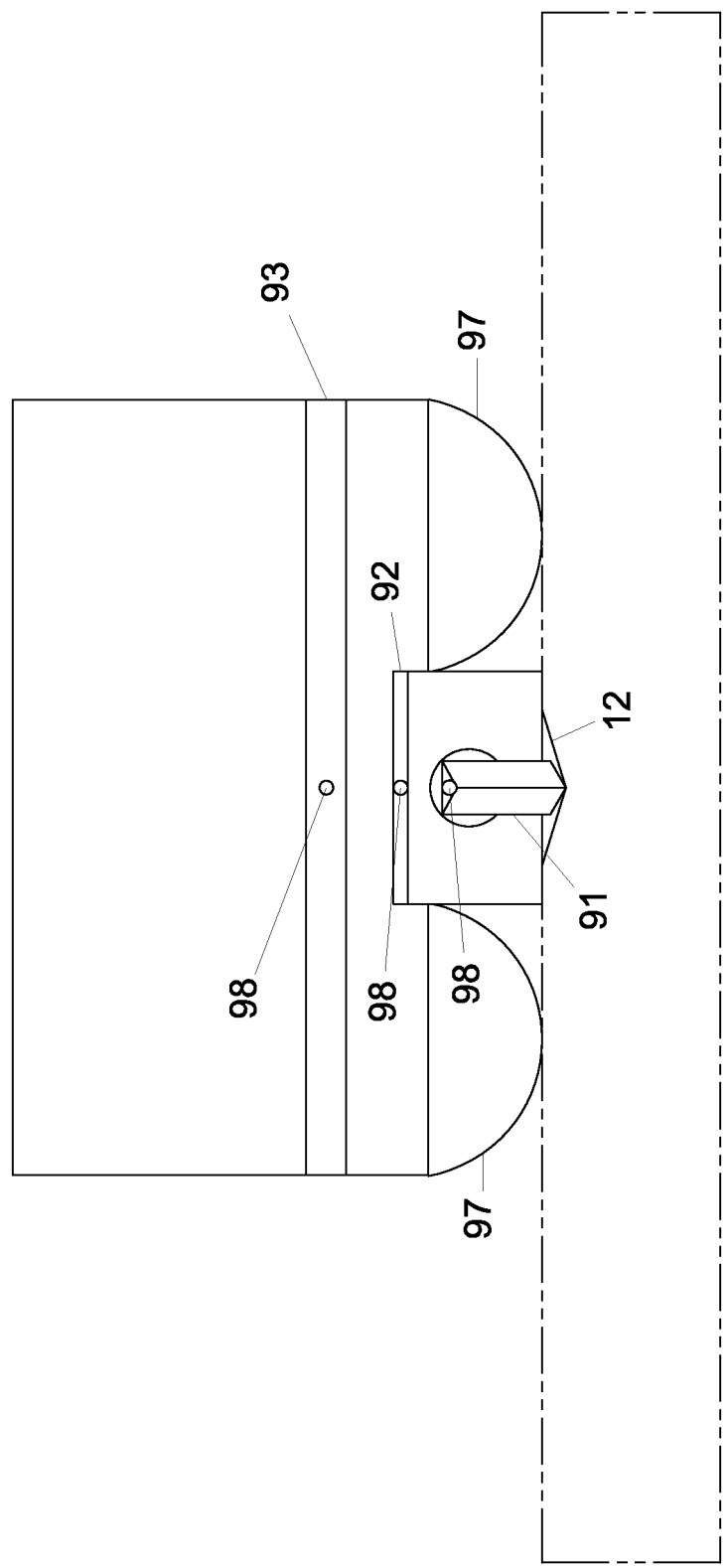
Figure 18B:
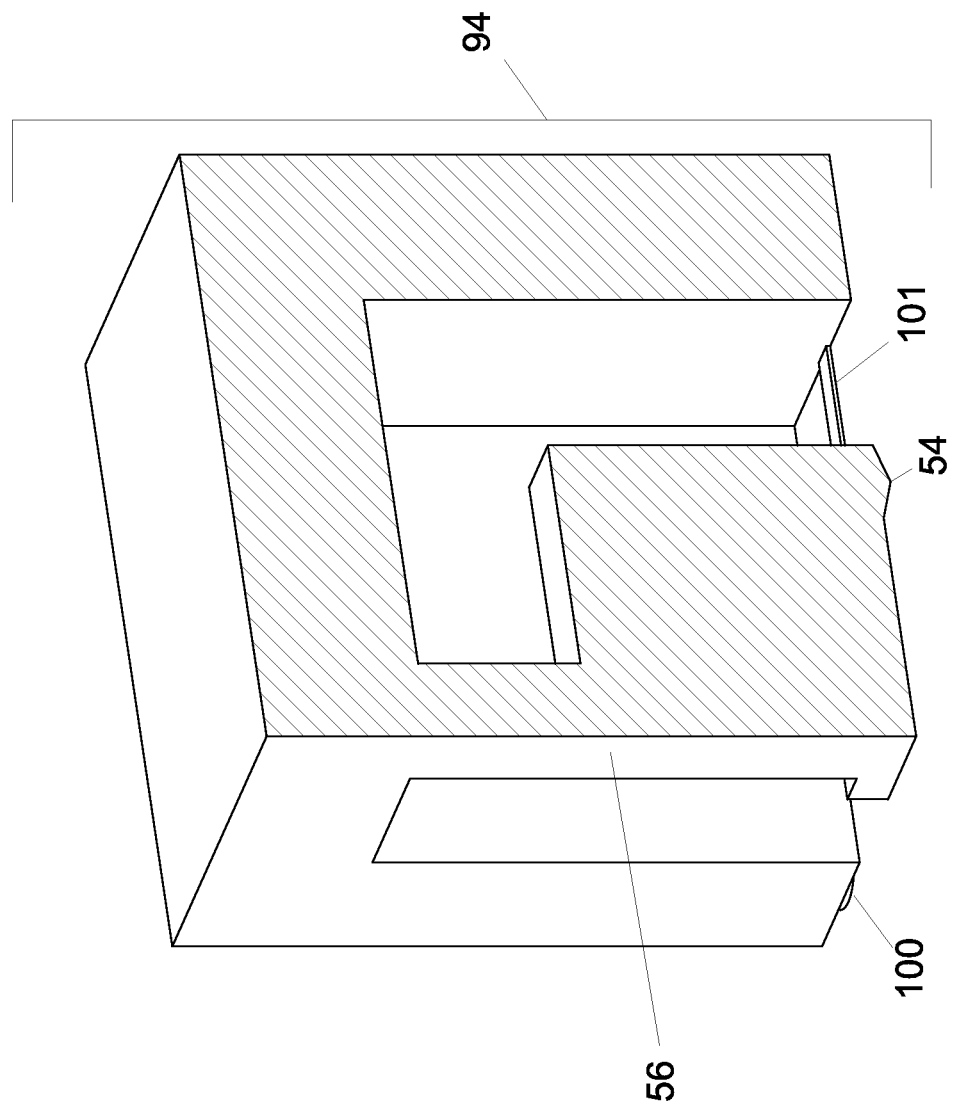
Figure 18C:
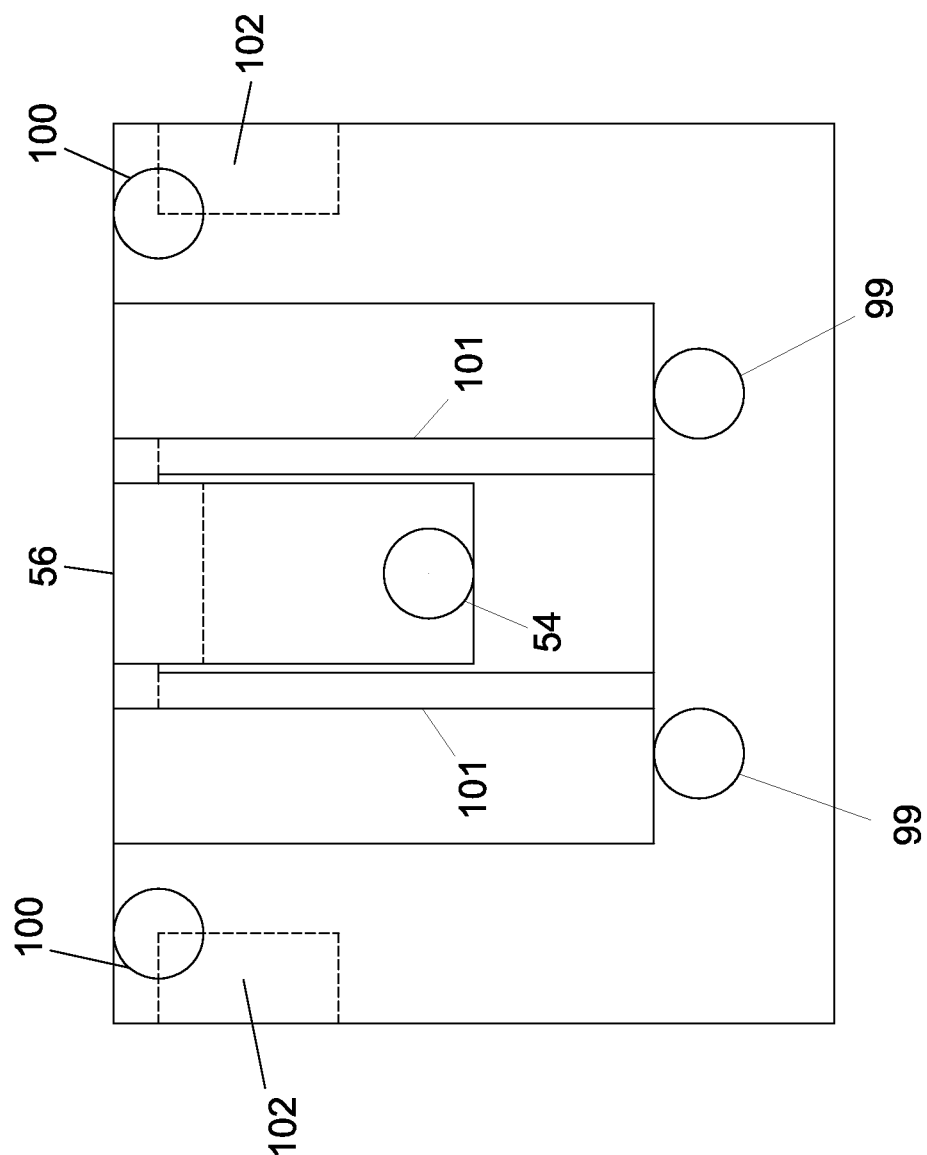
Figure 19A:
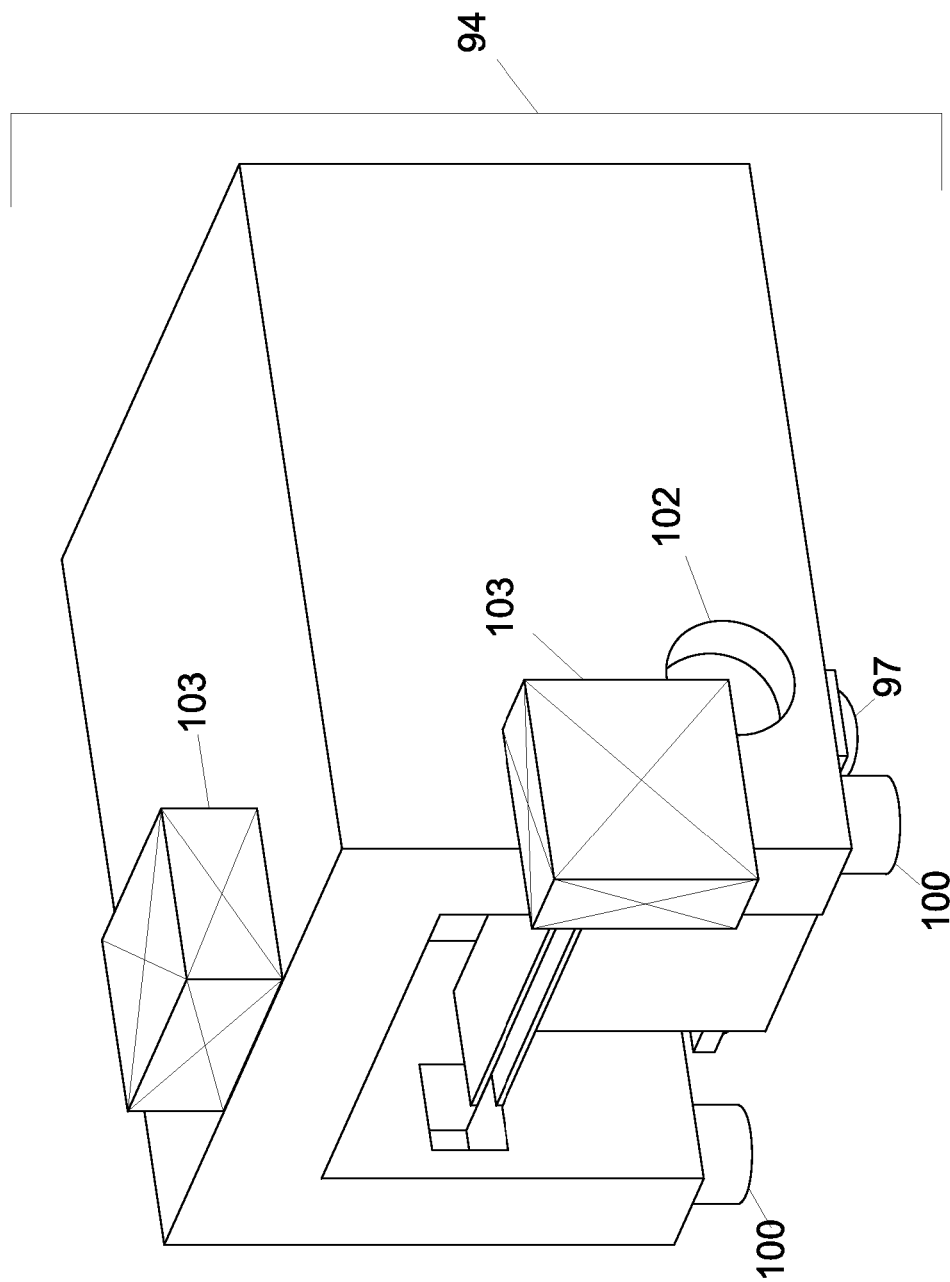
FIGS. 19A-C depict various schematic views of an exemplary integrated testing apparatus and profile monitoring apparatus.
Figure 19B:
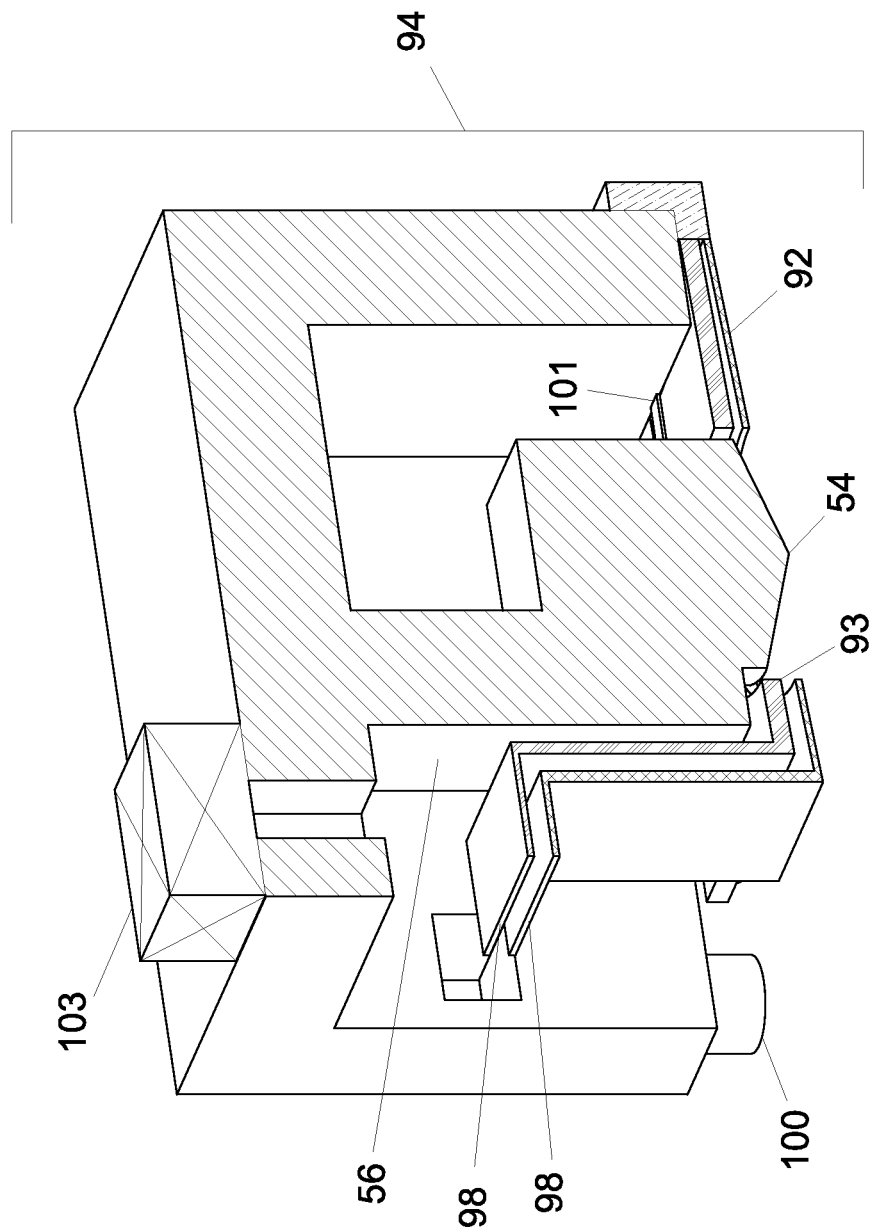
Figure 19C:
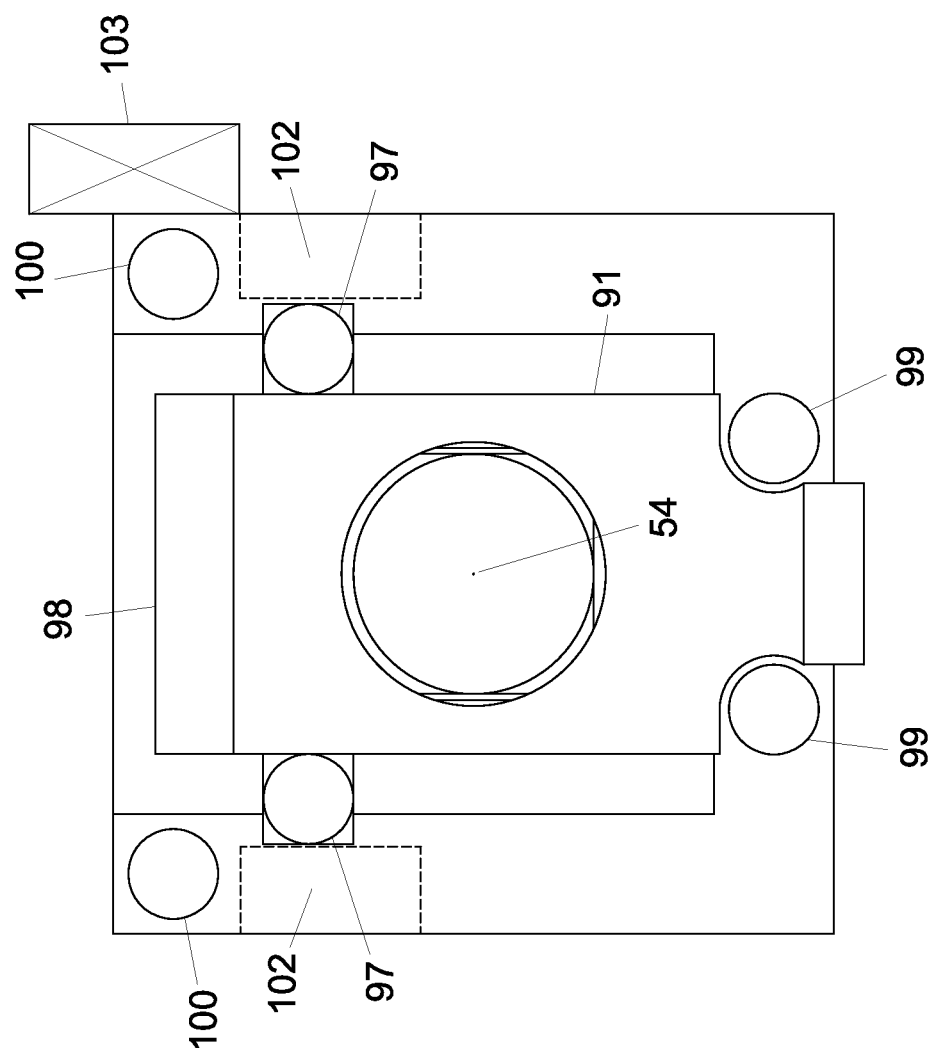

As shown in FIGS. 16 and 17A-D, a profile monitoring apparatus 90 allows for monitoring additional information about the residual scratch profile. According to one embodiment, the profile monitoring apparatus 90 may include a combination of tracers. The tracers may be separate or combined by branching off from a larger tracer or another apparatus. A scratch center tracer 91 allows for monitoring the scratch depth, and the scratch center tracer may have a smaller included angle than the angle at the center of the residual scratch profile, as shown in FIG. 16. The scratch center tracer 91 may also identify and measure surface roughness and local variations caused by pores, inclusions and micro cracks in the material. A pile-up height tracer 92 may be similar to the one shown in FIG. 12, but is utilized in conjunction with a surface referencing tracer 93. The pile-up height tracer 92 and the surface referencing tracer 93 may be sufficiently compliant under torsion to ensure contact on both sides of the scratch even in the presence of tilt. All tracers may be elastically preloaded to ensure sufficient contact pressure when the testing apparatus engages with the sample surface. In addition, the contact pressure may be induced through other mechanisms—e.g., self-weight and air pressure. The pile-up tracer may have a pile-up contact protrusion 80, a pile-up tracer corner 96, or a straight end. The surface referencing tracer 93 may have surface referencing tracer floats 97 and/or a straight end.

The tracers which are a part of the profile monitoring apparatus may be monitored through electronic methods, optical methods, mechanical methods and the like. Electrical methods may include monitoring capacitance, inductance, and/or piezo-electric properties. Optical methods may include confocal and optical micrometry with the light source illuminating from any suitable direction—e.g., from the top or side. Mechanical methods may include the use of an LVDT and other displacement transducers. According to one embodiment, the instrumentation may be mounted to the surface referencing tracer. An additional embodiment includes a tracer extension 98 for use with optical methods. Tracer extensions 98 may be mounted to the scratch center tracer 91, the pile-up height tracer 92, and/or the surface referencing tracer 93 to be used as reliable reference point for monitoring and measuring the profiles. Alternatively, the end of the tracers may be flat, even with optical methods such as with the use of confocal lenses.

As an alternative to the profile monitoring apparatus 90, a 2D profilometer, either contact-based or optical, may be mounted to the testing apparatus behind the tip. The 2D profilometer may allow for a full description of the scratch profile, including referencing the surface.

FIGS. 18A-C and 19A-C show an example of an integrated testing apparatus 94 and profile monitoring apparatus 90. The integration apparatus may include floats on the same support structure that supports the indentor tip column 56. A tilt correction function is shown in FIG. 16C with four floats 58. The number of floats need not be of a particular value, and may be adjusted based on the application. For example, there may be at least 1 float—e.g., at least 2, 3, 4, 5, 6, or more. Two of the floats may be located closer to each other to avoid an intermittent three point contact. The two floats located closer together are shown at the front of the device, but may be located at the back of the device. The configuration shown in FIG. 16C provides more room for the profile monitoring apparatus 90. To correct for surface curvature, the span length between the indentor tip 54 and the front floats 99 and the span length between the tip and the rear floats 100 may be set at a predetermined ratio. The testing apparatus 94 may include one or more tension ties 101 to carry the tangential contact force between the tip and the material surface. The testing apparatus 94 may be machined from a block, manufactured by etching methods, or constructed using 3D printing techniques, including laser sintering. A 3D printing method may be employed to form the testing apparatus from titanium. Other materials and fabrication techniques are also possible. The testing apparatus 94 may be formed from a unitary block of material. In one embodiment, the testing apparatus may include a force module and a profile monitoring apparatus, as described above, and the force module and the profile monitoring apparatus, together with the surface-referencing device, may be integrated in one body, such as a unitary block of material. According to one embodiment, the testing apparatus 94 may include a support structure formed from a unitary block of material. The unitary block of material may be formed by any suitable process—e.g., machining a block of material or building up the block of material through 3D printing. Portions of the testing apparatus 90 may have a surface coating or treatment providing increased wear resistance. The testing apparatus 90 may also include load transfer points 102 with the drive system to maximize stability. The load transfer points 102 may be set between the tip and the rear floats to help distribute the load between the floats 58. The testing apparatus 94 may also include surface profile probe mounts 103 located on the side, bottom, and/or the top of the core apparatus.

In the integrated apparatus, the profile monitoring apparatus 90 may be mounted after the tip is installed. The profiles for the tracers may span from the front of the device towards the back and across the tip, and may have sufficient compliance to accommodate the entirety of a measurement range. As shown in FIG. 16B, the rear end of the testing apparatus 94 may be extended to host the tracers, protecting the tracers from potential damage and providing locations for monitoring and measuring the tracer position.

FIG. 20 shows an apparatus including a surface preparation mechanism 107 in one embodiment. The apparatus may include a surfacing tool 104 mounted with or without a surface tool tilt 105 to engage the sample material as guided by a surfacing referencing device 106. The surfacing referencing device 106 may include a guided tool set having a set curvature. The surface preparation may introduce a predetermined curvature to the surface of the material sample, which may be corrected for by the surfacing referencing device. For example, a material sample curvature introduced by the surface preparation may be corrected for by actuating floats. The surface preparation allows for smooth transitions from the reference material to a weld. Surface preparation mechanisms 107 may be based on abrasive techniques or machining—e.g., such as end milling. The detail of the surfacing tool and the curvature of the surfacing referencing device 106 may be employed as an input to adjust the ratio of the span between the tip and the front floats 99 to the span between the tip and the rear floats 100.

Surface preparation is optional. In general, any type of processing to precondition the surface of the sample may be considered surface preparation. In one embodiment, the surface preparation allows verifying and/or improving at least one condition of the material surface before a scratch test is performed. In one embodiment, the surface preparation includes modifying a condition of the sample surface by using a guided tool set to engage the sample material and generate a pre-determined curvature. The decision of whether to perform surface preparation may be influenced by the material to be tested and the verification of the material surface condition. According to one embodiment, the material surface may be lubricated to reduce the friction of the material surface and/or the variation of the friction of the material surface.

The testing apparatus may be employed for the characterization of surfaces up to the toe of and through fillet and groove welds. For such an application, the floats 58 may be located behind the indentor tip 54. According to one embodiment, two floats 58 may be located a few scratch width distances behind the indentor tip 54. This arrangement allows the indentor tip 54 to approach a sloped portion of the weld. In some cases, two operations may be utilized to obtain the scratch profile information up to the end of the trajectory of the indentor tip 54 when the floats are located behind the indentor tip 54. A first operation includes the formation of the scratch with the tilt control concept, and a second operation may include monitoring the scratch profile using surface referencing. Transverse markers may be added on the surface of the material prior to forming the scratch to establish a relationship between the normal contact force response and the residual scratch profile. To combine the two operations, the profile monitoring apparatus may be mounted in the opposite orientation than shown in FIGS. 15, 16 and 17A-D. For example the profile monitoring apparatus may be attached at the rear of the apparatus and the contact with the surface profile may be just behind the indentor tip 54.

The testing apparatus may be connected to, or include, an analysis system that is configured to predict or estimate the physical properties of the material sample 10 based on the measured data produced during the scratch test. The analysis system may be a computing device. According to one embodiment, the testing apparatus may be connected to an analysis system by a wired connection, wireless connection, and/or a USB connection. Other types of connections are also possible.

The testing apparatus 30 as described above provides a simple-to-implement and reliable method of performing an instrumented scratch test to determine mechanical properties of materials. The testing apparatus 30 is capable of performing a scratch test experiment and measuring all of the inputs needed to predict mechanical properties using developed algorithms. Further, through the use of the surface-referencing device 40, the testing apparatus 30 may maintain a constant scratch depth throughout a scratch experiment. The surface-referencing device 40 may also be utilized to monitor the undeformed sample surface or control the elevation and alignment of the indentor tip through multiple methods. The testing apparatus may control the normal and translational forces accurately control the depth of the scratch during a scratch test experiment.

The testing apparatus as described above is a relatively compact mechanism that is suitable for attachment to both portable and stationary drive systems. This would allow for in-situ field testing of larger structures with a portable device or laboratory testing of smaller samples with a stationary drive system. The testing apparatus is capable of operating in either a push configuration or a pull configuration and may be utilized with multiple drive systems based on the desired scratch depth, normal load and testing sample geometry.

The testing apparatus described herein is able to continuously measure the reaction force at the indentor during a scratch experiment. The testing apparatus includes instrumentation to continuously measure the pile-up height or pile-up width along the length of the scratch through both contact and non-contact methods.

Although the description contains the above specificities, these should not be construed as limiting the scope of the invention, but as merely providing illustrations of some of the presently preferred embodiments of this invention. For example, the apparatus described may be incorporated within a continuous quality control system where scratches are used to monitor changes in material properties throughout production, such as a metal fabrication shop or automotive manufacturer. It is noted that any of the components of the apparatuses described herein, or any of the steps of the methods described herein using the apparatuses described herein, may be operated manually or by a computing device. The operation by a computer device may, for example, be carried out through the execution of the computing device by an algorithm (such as through a computer program). Similarly, the algorithms described herein may be computer algorithms stored as software on a non-transitory computer-readable medium. A computing device may refer to any device that comprises a processor. In addition, the assembly may be manufactured from a variety of materials including aluminum and brass, with various polymer covers to house the important instrumented components. The core device and associated support components may be made smaller or larger based on the desired scratch depth, applied load, and testing geometry. The drive system may exist in many different embodiments such that it may be attached to portable or stationary systems. The apparatus described herein may be packaged as modular units to offer specific features such as enhanced resolution or different scratch depths. The scratch width may be monitored in lieu of the method for measuring pile-up height specifically detailed above. According to one embodiment, the scratch parameters may be monitored by an independent sensing head that is located behind, and follows, the indentor. Also, the system may include an optional surface preparation module by milling, grinding or polishing. Additionally, the methods described herein may further including using equations derived from a computer simulation, such as finite element analysis, to establish predictors for the yield strength, the strain hardening exponent, the ultimate tensile strength, and/or an index of the elongation at break. Other analytical methods, such as analytical algorithms, may be employed to derive material property parameters.

Additional Notes

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

While various inventive embodiments have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments of the invention may be implemented in any of numerous ways. For example, some embodiments may be implemented using hardware, software or a combination thereof. When any aspect of an embodiment is implemented at least in part in software, the software code may be executed on any suitable processor or collection of processors, whether provided in a single computer or distributed among multiple computers.

In this respect, various aspects of the invention may be embodied at least in part as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology discussed above. The computer readable medium or media may be transportable, such that the program or programs stored thereon may be loaded onto one or more different computers or other processors to implement various aspects of the present technology as discussed above.

The terms "program" or "software" are used herein in a generic sense to refer to any type of computer code or set of computer-executable instructions that may be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." Any ranges cited herein are inclusive.

The terms "substantially" and "about" used throughout this Specification are used to describe and account for small fluctuations. For example, they may refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed:

1. An apparatus for performing a frictional sliding test on a sample, the apparatus comprising:
   an indentor wherein a tip thereof is configured to engage a sample surface at a contact location forming a slope between the indentor and the sample surface;
   a surface-referencing device configured to control the slope of the indentor relative to the sample surface at the contact location as the indentor travels during the frictional sliding test in order to provide tilt correction;
   a drive mechanism configured to cause the indentor to move along the sample surface to form a scratch;
   a measurement device configured to measure a pile-up height of sample material removed from the scratch, a depth of the scratch, and/or a width of the scratch; and
   a support structure configured to support the indentor, the surface-referencing device, and the measurement device.

2. The apparatus of claim 1, wherein the measurement device is configured to measure the pile-up height of the sample material removed from the scratch, the depth of the scratch and/or the width of the scratch simultaneously with the formation of the scratch.

3. The apparatus of claim 1, wherein the drive mechanism is attached to the support structure, such that the drive mechanism is configured to move the support structure along the sample surface.

4. The apparatus of claim 1, wherein the support structure is further configured to contact the sample surface and to move over the sample surface.

5. The apparatus of claim 1, further comprising a normal load application mechanism configured to apply a normal load to the indentor.

6. The apparatus of claim 1, further comprising a force probe configured to measure a force or load, including a normal force, between the indentor and the sample surface.

7. The apparatus of claim 1, wherein the drive mechanism comprises an attachment mechanism configured to fixedly attach the drive mechanism to the sample surface.

8. The apparatus of claim 1, wherein the drive mechanism comprises an attachment mechanism that comprises at least one electromagnet.

9. The apparatus of claim 1, further comprising technology for monitoring the elevation of the sample surface along a trajectory of the indentor, the monitoring technology including contactless sensors based on optics, capacitance, or inductance, and displacement probes, including leaf springs and linear voltage displacement transducers (LVDTs).

10. The apparatus of claim 1, wherein the apparatus is portable.

11. The apparatus of claim 1, further comprising a force module and a profile monitoring apparatus, wherein the force module, the surface-referencing device, and the profile monitoring apparatus are integrated in one body.

12. A method for performing a frictional sliding test on a sample surface, the method comprising:
   providing the apparatus of claim 1;
   engaging the indenter with the sample surface;
   establishing a position of the indenter relative to the sample surface as the indenter travels;
   moving the indenter along the sample surface to form a scratch; and
   measuring a pile-up height of sample material removed from the scratch, a depth of the scratch, and/or a scratch width,
   wherein the forming and measuring are carried out simultaneously or sequentially.

13. The method of claim 12, further comprising measuring a normal load on the indentor.

14. The method of claim 12, further comprising measuring a position of the indentor relative to the sample surface.

15. The method of claim 12, further comprising maintaining a constant normal load on the indentor.

16. The method of claim 12, further comprising maintaining a constant displacement of the indentor relative to the sample surface in a normal direction.

17. The method of claim 12, further comprising calculating scratch hardness, indentation hardness, yield strength, ultimate testing strength, strain hardening behavior and/or elongation at break of the material forming the sample surface based on the measured pile-up height, depth of the scratch, and/or scratch width.

18. The method of claim 12, further comprising applying a normal load to the indentor.

19. The method of claim 12, wherein the attachment mechanism comprises an electromagnet.

20. The method of claim 12, wherein the support structure includes at least one float that is configured to contact the sample surface and to allow the support structure to move over the sample surface.

21. The method of claim 12, further comprising preparing the sample surface before forming the scratch.

22. The method of claim 21, wherein preparing the sample surface comprises removing at least a portion of the sample surface.

23. The method of claim 12, wherein the sample surface includes a curvature introduced by preparing the sample surface, the method further comprising correcting for the curvature of the sample surface during the moving of the indentor to form the scratch and during the measuring.

24. The method of claim 12, further comprising modifying a condition of the sample surface by using a guided tool set to engage the sample material and generate a predetermined curvature.

25. The method of claim 12, further comprising analyzing the scratch to determine physical properties of a material sample being tested.

26. The apparatus of claim 1, further configured to operate in a monitor mode, in which the surface-referencing device is configured to establish an elevation of the sample surface along a trajectory of the indentor.

27. The apparatus of claim 1, further configured to operate in a control mode, in which elevations of surface-referencing members of the surface-referencing device are maintained at the same value.

* * * * *